(12) United States Patent
Peshoff

(10) Patent No.: US 6,660,306 B2
(45) Date of Patent: Dec. 9, 2003

(54) WOUND HEALING COMPOUND

(76) Inventor: Mickey L. Peshoff, 619 Cypress St., Suite B, Sulphur, LA (US) 70663

( * ) Notice: Subject to any disclaimer, the term of this patent is extended or adjusted under 35 U.S.C. 154(b) by 0 days.

(21) Appl. No.: 10/125,165

(22) Filed: Apr. 18, 2002

(65) Prior Publication Data

US 2002/0114847 A1 Aug. 22, 2002

Related U.S. Application Data

(63) Continuation-in-part of application No. 09/689,087, filed on Oct. 12, 2000, now abandoned.

(51) Int. Cl.$^7$ .................... A61K 31/4174; A61K 33/30; A61K 38/16

(52) U.S. Cl. ..................................... 424/642

(58) Field of Search ................. 424/641, 642, 424/DIG. 13; 514/6, 167, 168, 396, 458, 494, 552, 681, 725, 763, 859, 862, 864, 865, 886, 887, 904, 905

(56) References Cited

U.S. PATENT DOCUMENTS 6,071,541 A * 6/2000 Murad .................. 424/616
6,479,058 B1 * 11/2002 McCadden .................. 424/401

FOREIGN PATENT DOCUMENTS

EP          564804        * 10/1993

* cited by examiner

*Primary Examiner*—John Pak
(74) *Attorney, Agent, or Firm*—Keaty Professional Law Corporation

(57) ABSTRACT

This invention pertains to therapeutic antibacterial/antifungal-wound healing compositions comprise a therapeutically effective amount of antibacterial agents and/or antifungal agents and/or wound healing composition alone. In one embodiment, the wound healing composition comprises (a) zinc oxide and (b) fat-soluble vitamins. The therapeutic antibacterial/antifungal-wound healing compositions may be utilized in a wide variety of pharmaceutical products. This invention also relates to methods for preparing and using the antibacterial/antifungal-wound healing compositions and the pharmaceutical products in which the therapeutic compositions may be used.

7 Claims, No Drawings

WOUND HEALING COMPOUND

This application is a continuation-in-part of U.S. patent application Ser. No. 09/689,087, filed on Oct. 12, 2000, now abandoned.

FIELD OF INVENTION

This invention pertains to therapeutic antibacterial/antifungal-wound healing compositions useful for reducing the size, duration, and severity of wounds both infected and non-infected. More particularly, the antibacterial/antifungal-wound healing compositions comprise an antibacterial agent and/or, an antifungal agent, and a therapeutic wound healing composition and/or its metabolites. A preferred embodiment of the therapeutic wound healing composition of this invention comprises (a) zinc oxide and, (b) an admixture of two or more of the four fat soluble vitamins.

BACKGROUND OF INVENTION

Wound Healing

Wounds are internal or external bodily injuries or lesions caused by physical means, such as mechanical, chemical, viral, bacterial, fungal and other pathogenic organisms, or thermal means, which disrupt the normal continuity of tissue structures. Such bodily injuries include contusions, wounds in which the skin is unbroken, incisions, wounds in which the skin is broken cutting instrument, and lacerations, wounds in which the skin is broken by a dull or, blunt instrument. Wounds may be caused by accident, surgery, pathological organisms, or by surgical procedures. Patients who suffer wounds could benefit from an antibacterial/antifungal-wound healing composition.

Wound healing consists of a series of processes whereby injured tissue is repaired, specialized tissue is regenerated, and new tissue is reorganized. Wound healing consists of three major phases: a) an inflammation stage (0–3 days), proliferation stage (3–12 days), and a remodeling phase 3 days to 6 mos).

During the inflammation phase, platelet aggregation and clotting from a matrix which traps the plasma proteins and blood cells to induce the influx of various types of cells. During the cellular proliferation phase, new connective or granulation tissue and blood vessels are formed. During the remodeling phase, granulation tissue is replaced by a network of collagen and elastin fibers leading to the formation of scar tissue.

When cells are injured or killed as the result of a wound, a wound healing step is desirable to resuscitate the injured cells and produce new cells to replace the dead cells. The healing process requires the reversal of cytotoxicity, the suppression of inflammation, and the stimulation of cellular viability and proliferation. Wounds require low levels of oxygen in the initial stages of healing to suppress oxidative damage and higher levels of oxygen in the later stages of healing to promote collagen formation by fibroblasts.

Mammalian cells are continuously exposed to activate oxygen species such as superoxide ($O_2^-$), hydrogen peroxide ($H_2O_2$), hydroxyl radical (OH), and singlet oxygen ($^1O_2$). In vivo, these reactive oxygen intermediates are generated by cells in response to aerobic metabolism, catabolism of drugs and other xenobitics, ultraviolet and x-ray radiation, and the respiratory burst of phagocytic cells (such as white blood cells) to kill invading bacteria such as those introduced through wounds. Hydrogen peroxide, for example, is produced during respiration of most living organisms especially by stressed and injured cells.

These active oxygen species can injure cells. An important example of such damage is lipid peroxidation which involves the oxidative degradation of unsaturated lipids. Lipid peroxidation is highly detrimental to membrane structure and function and can cause numerous cytopathological effects. Cells defend against lipid peroxidation by producing radical scavengers such as superoxide dismutase, catalase, and peroxidase. Injured cells have a decreased ability to produce radical scavengers. Excess hydrogen peroxide can react with DNA to cause backbone breakage, produce mutations, and alter and liberate bases. Hydrogen peroxide can also react with pyrimidines to open the 5,6-double bond, which reaction inhibits the ability of pyrimidines to hydrogen bond to complementary bases, Hallaender et al. (1971). Such oxidative biochemical injury can result in the loss of cellular membrane integrity, reduced enzyme activity, changes in transport kinetics, changes in membrane lipid content, and leakage of potassium ions, amino acids, and other cellular material.

Antioxidants have been shown to inhibit damage associated with active oxygen species. For example, pyruvate and other Alpha-keotacids have been reported to react rapidly and stoichiometrically with hydrogen peroxide to protect cells from cytolytic effects, O'Donnell=Tormey et al., J. Exp. Med., 165, pp. 500–514 (1987).

SUMMARY OF THE INVENTION

This invention pertains to therapeutic antibacterial/antifungal-wound healing compositions for reducing the size, duration, and severity of wounds both infected and non-infected. The compositions of the invention comprise a therapeutically effective amount of one or more antibacterial agents and/or, one or more antifungal agents, and a wound healing composition. A preferred embodiment of the wound healing composition of this invention comprises (a) zinc oxide and, (b) an admixture of two or more of the four fat soluble vitamins. The therapeutic antibacterial/antifungal-wound healing compositions of this invention may be utilized in a wide variety of pharmaceutical products.

This invention also comprises augmented therapeutic antibacterial/antifungal-wound healing compositions comprising antibacterial agents, antifungal agents, and a therapeutic wound healing composition in combination with one or more medicament. This invention also relates to methods for preparing and using the augmented therapeutic antibacterial/antifungal-wound healing compositions and the pharmaceutical products in which the augmented compositions may be used.

DETAILED DESCRIPTION OF INVENTION

This invention pertains to antibacterial/antifungal-wound healing compositions which comprise one or more antibacterial agents, one or more antifungal agents, and a wound healing composition or its metabolites. In one embodiment the wound healing composition comprises (a) zinc oxide and (b) an admixture of two or more of the four fat soluble vitamins.

Applicant has discovered therapeutic wound healing compositions for preventing and reducing injuries to mammalian cells and increasing the resuscitation rate of injured mammalian cells. Wounds treated with the therapeutic wound healing composition showed significantly improved wound closing and healing one untreated over untreated wounds and wounds treated by other means including other conventional wound healing compositions. The wound healing compositions may be used alone or with other medicaments.

The therapeutic wound healing compositions of this invention are Embodiment One. There are several aspects of Embodiment One of therapeutic wound healing compositions in this invention. In a first aspect, (I.A), the therapeutic wound healing composition comprises (a) zinc oxide and (b) an admixture of two or more of the four fat soluble vitamins.

The therapeutic wound healing compositions of this invention are further combined with a therapeutically effective amount of antibacterial agent (X) and/or a therapeutically effective amount of antifungal (Y) to form the antibacterial/antifungal-wound healing compositions (I.A-X+Y). The antibacterial/antifungal-wound healing compositions may be alone or in combination with other medicaments. This invention also pertains to methods for preparing and using the antibacterial/antifungal-wound healing compositions and the pharmaceutical products in which the therapeutic compositions may be used.

The therapeutic antibacterial/antifungal-wound healing compositions of this invention may be further combined with one or more additional medicaments for treating wounds to form augmented antibacterial/antifungal-wound healing compositions. This invention also relates to methods for preparing and using the augmented therapeutic antibacterial/antifungal-wound healing compositions and the pharmaceutical products in which the augmented compositions may be used.

The term "injured cell" as used herein means a cell that has any activity disrupted for any reason. For example, an injured cell may be a cell that has injured membranes or damaged DNA, RNA, and ribosomes, for example, a cell which has (a) injured membranes so that transport through the membranes is diminished resulting in an increase in toxins and normal cellular wastes inside the cell and a decrease in nutrients and other components necessary for cellular repair inside the cell (b) an increase in concentration of oxygen radicals inside the cell because of the decreased ability of the cell to produce antioxidants and enzymes, or (c) damaged DNA, RNA, and ribisomes which must be repaired or replaced before normal cellular functions can be resumed. The term "resuscitation" of injured mammalian cells as used herein means the reversal of cytotoxicity, the stabilization of the cellular membrane, an increase in the proliferation rate of the cell, and/or the normalization of cellular functions such as the secretion of growth factors, hormones, and the like. The term "cytotoxity" as used herein means a condition caused by a cytotoxic agent that injures the cell. Injured cells do not proliferate because injured cell expend all energy on cellular repair. Aiding cellular repair promotes cellular proliferation.

The term "precursor", as used herein, refers to compounds which undergo biotransformation prior to exhibiting their pharmacological effects. The chemical modification of drugs to overcome pharmaceutical problems has also been termed "drug latentiation." Drug latentiation is the chemical modification of a biologically active to form a new compound which upon in vivo/vitro enzymatic attack will liberate the parent compound. The chemical alterations of the parent compound are such that the change in physiochemical properties will affect the absorption, distribution, and enzymatic metabolism. The definition of drug latentiation has also been extended to include nonenzymatic regeneration of the parent compound. Regeneration takes place as a consequence of hydrolytic, disassociative, and other reactions not necessarily enzyme mediated. The terms precursor, prodrugs, latentiated drugs, and bioreversible derivatives are used interchangeably. By inference, latentiation implies a time lag element or time component involved in regenerating the bioactive parent molecule in vivi. The terms prod rug and precursor are general in that they include latentiation drug derivatives as well as those substances which are converted after administration to the actual substance which combines with receptors. The term prod rug is a generic term for agents which undergo biotransformation prior to exhibiting their pharmacological actions. In the case where the administered drug is not the active agent, but is rather biotransformed to the active agent. The term prod rug also includes compounds which may not necessarily undergo biotransformation to the administered drug but may undergo biotransformation to the active agent which exhibits the desired pharmacological effect.

The term "metabolite", as used herein, refers to any substance produced by the metabolism or by a metabolic process. Metabolism, as used herein, refers to the various chemical/biochemical reactions involved in the transformation of molecules or chemical compounds occurring in the cells therein.

I. Wound Healing Compositions

A. Embodiment One (I.A-F)

The cells which may be treated with the therapeutic wound healing compositions in the present invention are mammalian cells. Although applicant will describe the present therapeutic wound healing compositions as useful for treating mammalian epidermal karatinocytes and mammalian monocytes, and cells of the subcutaneous tissues, and muscle tissues, and bone and applicant contemplates that the therapeutic wound healing compositions may also be used to protect or resuscitate all mammalian cells. Keratinocytes are representative of normal mammalian cells and are the fastest proliferating cells in the body. The correlation between the reaction of keratinocytes to injury and therapy and that of mammalian cell in general is very high. Monocytes are representative of specialized mammalian cells such as white blood cells in the immune system and the organ cells in the liver, kidney, heart, and brain. The mammalian cells may be treated in vivo or in vitro.

Epidermal keratinocytes are the specialized cell of the epidermis which synthesize keratin, a scleroprotein which is a principal constituent of epidermis, hair, nails, horny tissue, and the organic matrix of the enamel of teeth. Mammalian epidermal keratinocytes constitute about 95% of the epidermal cells and together with the melanocytes form the binary system of the epidermis. In its various successive stages, epidermal keratinoceyes are also known as basal cells, prickle cells, and granular cells. Monocytes are mononuclear leukocytes which undergo respiratory bursting and are involved in reactive oxygen mediated damage within the epidermis. Leukocytes are white blood cells or corpuscles which may be classified into two main groups: granular leukoceyes (granulocytes) which are leukocytes with abundant granules in the cytoplasm and nongranular leukocytes (nongranulocytes) which are leukocytes without specific granules in the cytoplasm and which include the lymphocytes and monocytes. Phagocyte cells are cells which ingest microorganisms or other cells and foreign particles. Monocytes are also known as large mononuclear leukocytes, and hyaline or transitional leukocytes.

Epidermal keratinocytic cells and monocytic cells have multiple oxygen generating mechanisms and the degree to which each type of mechanism functions differs in each type of cell. In monocytes, for example, the respiratory bursting process is more pronounced than in dermal keratinocytes. Hence, the components in the therapeutic wound healing composition may vary depending upon the types of cells involved in the condition being treated.

As set out above, in the first aspect of Embodiment One (I.A), the therapeutic wound healing composition for treating mammalian cells comprises (a) zinc oxide and, (b) all forms and presursors of Vitamin A and, (c) all forms and presursors of Vitamin D. In a second aspect of Embodiment One (I.B), the therapeutic wound healing composition for treating mammalian cells comprises (a) zinc oxide and, (b) all forms and precursors of Vitamin A and, (c) all forms and precursors of Vitamin D and, (d) all forms and precursors of Vitamin E. In a third aspect of Embodiment (I.C), the therapeutic wound healing composition for treating mammalian cells comprises (a) zinc oxide and, (b) all forms and precurors of Vitamin A and, (c) all forms and precursors of Vitamin D and, (d) all forms and precursors of Vitamin K. In a fourth aspect of Embodiment One (I.D), the therapeutic wound healing composition for treating mammalian cells comprises (a) zinc oxide and, (b) all forms and precursors of Vitamin A and, (c) all forms and precursors of Vitamin D and, (d) all forms and precursors of Vitamin E and, (e) all forms and precursors of Vitamin K. In a fifth aspect of Embodiment One (I.E), the therapeutic wound healing composition for treating mammalian cells comprises (a) all forms and precursors of Vitamin A and, (b) all forms and precursors of Vitamin D and, (c) all forms and precursors of Vitamin E. In a sixth aspect of Embodiment One (I.F), the therapeutic wound healing composition for treating mammalian cells comprises (a) all forms and precursors of Vitamin A and, (b) all forms and precursors of Vitamin D and, (c) all forms and precursors for Vitamin E and, (d) all forms and precursors of Vitamin K. In a seventh aspect of Embodiment One (I.G), the therapeutic wound healing composition for treating mammalian cells comprises (a) all forms and precursors of Vitamin A and, (b) all forms and precursors of Vitamin D and, (c) all forms and precursors of Vitamin K.

Zinc oxide has been shown to be an essential catalyst in many biochemical reactions. Zinc has been reported to display antibacterial effects. Zinc oxide has also been shown to maintain a constant level of zinc when applied to wounds as compared to salts of zinc. Re-epitheliaization is enhanced when zinc oxide is present. Inflammatory reaction has been shown to be reduced with adequate zinc concentration. Zinc oxide promotes cleansing of wounds and decreases deterioration of existing wounds. It has also been reported that the application of zinc oxide to wounds not only corrects the local zinc deficiency but also acts pharmacologically. Patients with diabetes mellitus have been noted as having zinc deficiencies related to impaired wound healing. Zinc oxide has also been shown to be effective in healing donor sites from skin grafting.

Application of zinc oxide has been shown to accelerate the healing of both chronic and acute wounds and increases endogenous gene expression of insulin-like growth factor-1 in granulation tissue.

Vitamin A plays an important role in the orderly differentiation of epithelium. The mechanism is not precisely understood, however in cell culture systems, Vitamin A regulates the gene expression of a number of cell receptors and secreted proteins, including receptors for growth factors. It is also reported that Vitamin A plays a role in the evolution of granulation tissue. Vitamin A have been shown to visibly accelerate wound healing after thermal injury including tissues which were previously believed to be irreparable. It has also been shown that Vitamin A accelerates epidermal cell and subcutaneous tissue as well as fibroblast proliferation after UV injury and these were shown to be dose related. Vitamin A has also been shown to be effective in the treatment of cancers, acne, and psoriasis and is essential for vision and occular tissue formation.

Vitamin D has been shown to be a potent agonist of the Vitamin D receptor which stimulates glycosaminoglycan synthesis and transforming growth factor -beta 1 (TGF-beta 1) thereby accelerating wound healing. Vitamin D has been shown to be an effective treatment for chronic leg wounds. It is reported that Vitamin D promotes dermal wound strength and re-epithelialization as well as enhancing granulation tissue formation. It has also been shown to be effective in preventing osteomyelitis. Vitamin D increases the absorption of calcium in mammalian cells. It can also prevent secondary hypothyroidism in elderly patients with renal insufficiency and has been shown to possibly prevent breast cancer. It has also been evidenced that Vitamin D may slow the progress of sub clinical to clinically significant prostate cancer. Deficiency of Vitamin D has been known to cause rickets and hypocalcemic seizures. Vitamin D is also a membrane antioxident. Vitamin D has also been shown to increase the absorption of magnesium and bone mineral contents in mammals and may improve prevention and treatment of renal osteodystrophy. There is a link reported between Vitamin D levels and the severity of rheumatoid arthritis with those patients with more severity of the disease are shown to be the most deficient in this important vitamin. Vitamin D and calcium deficiencies have been related to migraine headaches in post menopausal females. Vitamin D has also been shown to be a treatment for psoriasis.

Vitamin E has been shown to be effective in promoting enhanced fibrosis of tissues. It has also been shown to be an antioxidant. Muscle weakness, ataxia, sensory impairment, vision abnormalities, and dysarthria have been reported as due to Vitamin E deficiency. Vitamin E has also been shown to accelerate wound healing including gingival wounds. It has also been shown to prevent endothelial dysfunction associated with atherosclerosis and also been shown to show some promise in the impairment of carcinogenesis. Vitamin E has also been shown to depress the decline in immune response, and thereby decrease the incidence of neoplasm's and infections in the aged. Vitamin E has been shown to inhibit the growth of squamous cell carcinoma cells. It has also been suggested that Vitamin E levels may help determine the host resistance to parasite and viral infections. There is also epidemologic evidence that Vitamin E may reduce the risk of coronary heart disease and may be effective in the treatment of dermatitis and may be effective in combating tardive dyskinesia. Vitamin A has also been shown to prevent diabetes induced abnormal retinal blood flow. It has also been demonstrated that Vitamin E can prevent the activation of protein kinase C(PKC) and diacylglycerol (DAG) in blood vessels during hyperglycemia thus suppressing their negative effects on the vascular cells and tissues. Another study has shown that Vitamin E can slow the rate of motor decline in patients with Huntington's disease.

Vitamin K is an essential cofactor in the formation of a microsomal carboxlase that is necessary in converting glutamyl residues in certain protein precursors into gamma-carboxyglutamates which is required by clotting factors to cause clotting of blood. Vitamin K has also been shown to play an important role in bone metabolism and can be used to prevent loss of bone mass (osteoporosis). It has been reported that Vitamin K also displays antioxidant properties. Vitamin K may also be used as prophylaxis in high dose chemotherapy.

The amount of zinc oxide present in the therapeutic wound healing compositions of the present invention is a therapeutically effective amount. A therapeutically effective amount of zinc oxide is that amount of zinc oxide necessary for the inventive composition to reduce injury to mammalian cells or increase the resuscitation rate of injured mammalian cells or the amount necessary to aid or cause the proliferation of new cells including precursor cells. The exact amount of zinc oxide is a matter of preference subject to such factors as type of condition being treated as well as the other ingredients in the composition. In a preferred embodiment, zinc oxide is present in the therapeutic wound healing composition in an amount from about 0.01% to about 75%, preferably about 2% to about 25%, and more preferably about 5% to about 20%, by weight of the therapeutic wound healing composition.

The amount of the fat soluble vitamins present in the therapeutic wound healing compositions of the present invention is a therapeutically effective amount. A therapeutic all effective amount of fat soluble vitamins is the amount necessary to resuscitate and cause proliferation to injured mammalian cells. The exact amount of fat soluble vitamins is a matter of preference subject to such factors as the type of condition being treated as well as other ingredients in the composition. In a preferred embodiment, the fat soluble vitamins are present in the therapeutic wound healing composition in an amount from about 0.01% to about 100%, preferably from about 0.05% to about 40%, and more preferably from about 1% to about 35%, by weight of the therapeutic wound healing composition.

Antioxidants are substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. The antioxidants usefully in the present invention may be selected from the group consisting of all forms of Vitamin A (retinol), all forms of Vitamin.sub.2 (3,4-didehydroretinol), all forms of carotene such as Alpha-carotene,.beta.-carotene (beta, .beta.-carotene), gamma-carotene, deltacarotene, all forms of Vitamin C (D-ascorbic acid, L-ascorbic acid), all forms of tocopherol such as Vitamin E Alpha-tocopherol,34-dihydro-2,5,7,8-tetramethyl-2-(4,8,12-trimethyltridecyl)-2H-1-benzopy ran-6-o1), .beta.-tocopherol, gamma-tocopherol, delta-tocopherol, tocoquinone, tocotrienol, and Vitamin E esters which readily undergo hydrolysis to Vitamin E such as Vitamin E acetate and Vitamin E succinate, and pharmaceutically acceptable Vitamin E salts such as Vitamin E phosphate, prodrugs of Vitamin A, carotene, Vitamin C, and Vitamin E, pharmaceutically acceptable salts of Vitamin A, carotene, Vitamin C, and Vitamin E, and the like, and mixtures thereof. Preferably, the antioxidant is selected from the group of lipid-soluble antioxidants consisting of Vitamin A, .beta.-carotene, Vitamin E, Vitamin E acetate, and mixtures thereof. More preferably, the antioxidant is Vitamin E or Vitamin E acetate. Most preferably, the antioxidant is Vitamin E acetate.

The amount of antioxidant present in the therapeutic wound healing compositions of the present invention is a therapeutically effective amount. A therapeutically effective amount of antioxidant is that amount of antioxidant necessary for the inventive composition to prevent and reduce injury to mammalian cells or increase the resuscitation rate of injured mammalian cells. The exact amount of antioxidant is a matter of preference subject to such factors as the type of condition being treated as well as the other ingredients in the composition. In a preferred embodiment, the antioxidant is present in the therapeutic wound healing composition in an amount from about 0.1% to about 40%, preferably from about 0.2% to about 30%, and more preferably from about 0.5% to about 20%, by weight of the therapeutic wound healing composition.

In accord with the present invention, the therapeutic wound healing compositions of Embodiment One (IA.-F) for treating mammalian cells may be selected from the group consisting of:

(IA.) (a) zinc oxide; and
(b) all forms and precursors of Vitamins A; and,
(c) all forms and precursors of Vitamin D.
(I.B) (a) zinc oxide; and
(b) all forms and precursors of Vitamin A; and
(c) all forms and precursors of Vitamin D;
(d) all forms and precursors of Vitamin E.
(I.C) (a) zinc oxide; and
(b) all forms and precursors of Vitamin A; and
(c) all forms and precursors of Vitamin D; and
(d) all forms and precursors of Vitamin K.
(I.D) (a) zinc oxide; and
(b) all forms and precursors of Vitamin A; and
(c) all forms and precursors of Vitamin D; and
(d) all forms and precursors of Vitamin E; and
(e) all forms and precursors of Vitamin K.
(I.E) (a) all forms and precursors of Vitamin A; and
(b) all forms and precursors of Vitamin D; and
(c) all forms and precursors of Vitamin E.
(I.F) (a) all forms and precursors of Vitamin A; and
(b) all forms and precursors of Vitamin D; and
(c) all forms and precursors of Vitamin E; and
(d) all forms and precursors of Vitamin K.
(I.G) (a) all forms and precursors of Vitamin A; and
(b) all forms and precursor of Vitamin D; and
(c) all forms and precursors of Vitamin K.

Throughout this disclosure, applicant will suggest various theories or mechanisms by which applicant believes the components in the therapeutic wound healing composition and the antibacterial agents and antifungal agents function together in an unexpected synergistic manner to prevent and reduce injury to mammalian cells, increase the resuscitation rate of injured mammalian cells, and the proliferation of new cells. While the applicant may offer various mechanisms to explain the present invention, applicant does not want to be bound by theory. These mechanisms and theories are suggested to better understand the present invention but are not intended to limit the effective scope of the claims.

Accordingly the combination of ingredients set out in the above embodiments function together in an enhanced manner to prevent and reduce injury to mammalian cells and increase the resuscitation rate of injured mammalian cells and cause the proliferation of new cells. The therapeutic effects of the combination of the components in each of the above embodiments is markedly greater than that expected by the mere addition of the individual therapeutic components. Hence, applicant's therapeutic wound healing composition for treating mammalian cells have the ability to increase rates of cellular proliferation, increase cellular viability, increase cellular resistance to cytotoxic agents, and stop bleeding.

B. Methods for Making the Therapeutic Wound Healing Compositions of Embodiment One (I.A-G)

The present invention extends to methods of making the therapeutic wound healing compositions of Embodiment One (A.A-G). In general, a therapeutic wound healing composition is made by forming an admixture of the components of the composition. In a first aspect of Embodiment One (I.A), a therapeutic wound healing composition is made by forming an admixture of the components of a) zinc oxide b) Vitamin A and, c) Vitamin D. In a second aspect of Embodiment One (I.B), a therapeutic wound healing composition is made by forming an admixtures of a) zinc oxide, b) Vitamin A, c) Vitamin D, and d) Vitamin E. In a third aspect of Embodiment One (I.C), a therapeutic wound healing composition is made by forming an admixture of a) zinc oxide, b) Vitamin A, and c) Vitamin D, and, d) Vitamin K. In the fourth aspect of Embodiment One (I.D), a therapeutic wound healing composition is made by forming an admixture of a) zinc oxide, b) Vitamin A, c) Vitamin D, d) Vitamin E, and e) Vitamin K. In the fifth aspect of Embodiment One (I.E), a therapeutic wound healing composition is made by making an admixture of a) Vitamin A, b) Vitamin D, and c) Vitamin E. In a sixth aspect of Embodiment One (I.F), a therapeutic wound healing composition is made by forming an admixture of a) Vitamin A, b) Vitamin D, c) Vitamin E, and d) Vitamin K. In a seventh aspect of Embodiment One (I.G), a therapeutic wound healing composition is made by forming an admixture of a) Vitamin A, b) Vitamin D, and c) Vitamin K.

C. Methods for Employing the Wound Healing Compositions of Embodiment One (I.A)

The present invention extends to methods for employing the therapeutic wound healing compositions of Embodiment One (IA) in vivo and in vitro. In general, a therapeutic wound healing composition is employed by contacting the therapeutic composition with mammalian cells.

In the first aspect of Embodiment One (I.A), the invention is directed to a method for preventing and reducing injury to mammalian cells, and increasing the resuscitation rate of injured mammalian cells, which comprises the steps of (A) providing a therapeutic wound healing composition which comprises (a) zinc oxide and (b) all forms and precursors of Vitamin A, and (c) all forms and precursors of Vitamin D, and (B) contacting the therapeutic wound healing composition with the mammalian cells.

In the second aspect of Embodiment One (I.B), the invention is directed to a method of preventing and reducing injury to mammalian cells, and increasing the resuscitation rate of injured mammalian cells, which comprises the steps of (A) providing a therapeutic wound healing composition which comprises (a) zinc oxide and, (b) all forms and precursors of Vitamin A, (c) all forms and precursors of Vitamin D and, (c) all forms and precursors of Vitamin E and, (B) contacting the therapeutic wound healing composition with the mammalian cells.

In the third aspect of Embodiment One (I.C) the invention is directed to a method of preventing and reducing injury to mammalian cells, increasing the resuscitation rate of injured mammalian cells, and causing the flow of blood to decrease or cease at the wound site by causing it to coagulate, which comprises the steps of (A) providing the the therapeutic wound healing composition which comprises (a) zinc oxide and, (b) all forms and precursors of Vitamin A and, (c) all forms and precursors of Vitamin D and, (d) all forms and precursors of Vitamin K and, (B) contacting the therapeutic wound healing composition with the mammalian cells.

In the fourth aspect of Embodiment One (I.D) the invention is directed to a method of preventing and reducing injury to mammalian cells, increasing the resuscitation rate of injured mammalian cells, improving the remodeling phase of wound healing in mammalian cells, and causing the flow of blood to decrease or cease by causing it to coagulate at the wound site, which comprises the steps of (A) providing the therapeutic wound healing composition which comprises (a) zinc oxide and, (b) all forms and precursors of Vitamin A and, (c) all forms and precursors of Vitamin D and, (d) all forms and precursors of Vitamin E and, (e) all forms and precursors of Vitamin K and, (B) contacting the therapeutic wound healing composition with the mammalian cells.

In the fifth aspect of Embodiment One (I.E) the invention is directed to a method of preventing and reducing injury to mammalian cells, increasing the resuscitation rate of injured mammalian cells, and improving the remodeling phase of wound healing in mammalian cells, which comprises the steps of (A) providing the therapeutic wound healing composition which comprises (a) all forms and precursors of Vitamin A and, (b) all forms and precursors of Vitamin D and, (c) all forms and precursors of Vitamin E and, (B) contacting the therapeutic wound healing composition with the mammalian cells.

In the sixth aspect of Embodiment One (I.F) the invention is directed to a method of preventing and reducing injury to mammalian cells, increasing the resuscitation rate of injured mammalian cells, improving the remodeling phase of wound healing in mammalian cells, and causing the flow of blood to decrease or cease by causing it to coagulate at the wound site, which comprises the steps of (A) providing the therapeutic wound healing composition which comprises (a) all forms and precursors of Vitamin A and, (b) all forms and precursors of Vitamin D and, (c) all forms and precursors of Vitamin E and, (d) all forms and precursors of Vitamin K and, (B) contacting the therapeutic wound healing composition with the mammalian cells.

In a seventh aspect of Embodiment One (I.G) the invention is directed to a method of preventing and reducing injury to mammalian cells, increasing the resuscitation rate of injured mammalian cells, and causing the flow of blood to decrease or cease by causing it to coagulate at the wound site, which comprises the steps of (A) providing the therapeutic wound healing composition which comprises (a) all forms and precursors of Vitamin A and, (b) all forms and precursors of Vitamin D and, (c) all forms and precursors of Vitamin K and, (B) contacting the therapeutic wound healing composition with the mammalian cells.

In a preferred embodiment, the invention is directed to a method for healing a wound in a mammal which comprises the steps of:

(A) providing a therapeutic wound healing composition (I.A) which comprises:
  (a) zinc oxide; and
  (b) all forms and precursors of Vitamin A; and
  (c) all forms and precursors of Vitamin D; and
(B) contacting the therapeutic wound healing composition with the wound.

The types of wounds which may be healed using the wound healing compositions of Embodiment One (I.A-G) of the present invention are those which result from an injury which causes epidermal damage such as incisions, wounds in which the skin is broken by a cutting instrument, and lacerations, wounds by which the skin is broken by a blunt or dull instrument, and wounds of the skin caused by friction. The therapeutic compositions may also be used to treat dermatological disorders such as burns, Candidiasis and diaper rash, donor and receptor site wounds for skin transplants, ulcers (cutaneous, decubitus, venous stasis, sickle cell, and diabetic), psoriasis, skin rashes, and sunburn photo reactive process, and second and third degree burns. The topical therapeutic compositions may also be used orally in the form of a mouthwash or spray to protect or accelerate the healing of oral tissue such as mouth sores, bums, surgical sites, and ulcerations. The topical therapeutic compositions may further be used in opthomological preparations to treat wounds such as those which result from corneal ulcers, radialkeratotomy, corneal transplants, epikaratophakia and other surgically induced wounds in the eye. The thermorectal therapeutic compositions may be used in anorectal creams and suppositories to treat such conditions as pruritus, and proctitis, anal fissures, and hemorrhoids. In a preferred embodiment, the therapeutic compositions are used to treat wounds such as incisions and lacerations.

The wound healing compositions of Embodiment One (I.A-G) of the present invention may be utilized in topical products, ingestible products, and tissue culture medium to protect mammalian cells and increase the resuscitation rate of mammalian cells and enhance cell reproduction. For example, the therapeutic wound healing compositions may be used in topical skin care products to protect and increase the resuscitation rate of skin tissues such as in the treatment of various dermatological disorders such as photo-aging and sunburn photo-reactive processes. Injury of skin can occur for a variety of reasons. Injury often occurs to individuals who wash their hands often, to individuals who are exposed to stressful environmental conditions (overexposure to sunlight or chemical) or to the elderly or individuals with an underlying disease. The addition of the wound healing compositions to the present invention to a lotion provides a source of antioxidants to the skin which would protect the skin from the harmful effects of UV light, chemicals, and severe drying as well as healing the skin injured by these sources. The wound healing compositions may also be used for the following indications: a) Moisturizing and protecting; b) Healing dry cracked skin; c) healing irritated skin such as diaper rash; d) Healing severe dry skin due to other diseases (venous dermatitis); e) treating psoriasis and other hyperproliferative diseases; protecting skin from UV light damage (antioxident skin replacement and cell reproduction); treating seborrheic conditions; and h) treating shaving wounds in an after shave lotion.

The topical therapeutic wound healing compositions may also be used in the form of a mouth wash or a spray to protect and accelerate the healing of injured oral tissue such as mouth sores and bums. The topical therapeutic wound healing compositions may further be used in opthalmological preparations such as eye care products to neutralize hydrogen peroxide used in the cleaning of contact lenses. The topical therapeutic wound healing compositions may also be used in anorectal creams and suppositories to treat such conditions as pruritus ani, procitis, anal fissures, and hemorrhoids. Initially as white blood cells enter a wound site, the cells release oxygen radicals depleting the antioxidants at the wound site, thus impairing the healing process. Incorporating the wound healing compositions of the present invention into a wound healing formulation would facilitate healing by providing the site with usable antioxidants, and zinc oxide and vitamins A and D for cell resuscitation and reproduction. The wound healing compositions can be used for the following indications: a) Healing of cuts and scrapes; b) Burns; c) decubitus ulcers; d) bed sores, pressure ulcers; e) Fissures, Hemorrhoids; f) Used in combination with immunostimulators (stimulate healing in healing deficient mammals); g) Post surgical wounds including P&A's; h) bandages; i) Diabetic ulcerations; j) venous ulcerations; k) sickle cell ulcerations, and l) used in combination with wound cleansing agents. The wound healing compositions may also be used in ingestible products and increase the resuscitation rate of erosions, stomach ulcers, and hemorrhages in the gastric mucosa. Other injestible therapeutic products include: stroke medications; autoimmune disease medications; arthritis medications; ulcer medications; cancer medications (cytotoxic agents); heart medications to improve regional ventricular function and restore normal heart rate and pressure functions; lung medications to repair injured tissues; liver medication to suppress lipogenesis of alcoholic origin and prevent hepatic steatosis; kidney medication to suppress urinary calculi; detoxification medication to antagonize heavy metal poisoning, cyanide poisoning, sodium sulfide poisoning, other types of poisoning; and reduce and neutralize the production of oxygen radicals which produces tissue injury, to protect and further enhance the resuscitation rate of the injured mammalian cells. The therapeutic wound healing composition may be used in injestible products to treat inflammatory diseases such as hepatitis, gastritis, colitis, esophagitis, arthritis, and pancreatitis.

The therapeutic wound healing compositions of the present invention may also be used in tissue culture media and organ transplant media to reduce and prevent injury to mammalian cells and increase the resuscitation rate of injured mammalian cells. Tissue cultures and transplant organs encounter reactive oxygen species generated in the culture media by the injured cells. Organs particularly susceptible to oxidative damage during transport and transplantation due to reperfusion injury following ischemia are corneas, livers, hearts and kidneys. The therapeutic wound healing composition my be useful to abrobate reperfusion injury to such transplant organs as well as resuscitate and cause proliferation of cells.

In a specific embodiment, the invention is directed to a method for preserving mammalian cells in a culture medium which comprises steps of:

(A) providing a therapeutic wound healing composition selected from the group consisting of:

(IA.)
(a) zinc oxide; and
(b) all forms and precursors of Vitamins A; and
(c) all forms and precursors of Vitamin D.

(I.B)
(a) zinc oxide; and
(b) all forms and precursors of Vitamin A; and
(c) all forms and precursors of Vitamin D;
(d) all forms and precursors of Vitamin E.

(I.C)
(a) zinc oxide; and
(b) all forms and precursors of Vitamin A; and
(c) all forms and precursors of Vitamin D; and
(d) all forms and precursors of Vitamin K.

(I.D)
(a) zinc oxide; and
(b) all forms and precursors of Vitamin A; and
(c) all forms and precursors of Vitamin D; and
(d) all forms and precursors of Vitamin E; and
(e) all forms and precursors of Vitamin K.

(I.E)
(a) all forms and precursors of Vitamin A; and
(b) all forms and precursors of Vitamin D; and
(c) all forms and precursors of Vitamin E.

(I.F)
(a) all forms and precursors of Vitamin A; and
(b) all forms and precursors of Vitamin D; and
(c) all forms and precursors of Vitamin E; and
(d) all forms and precursors of Vitamin K.

(I.G)
(a) all forms and precursors of Vitamin A; and
(b) all forms and precursor of Vitamin D; and
(c) all forms and precursors of Vitamin K;

(B) providing mammalian cells in a culture medium; and (C) contacting the therapeutic wound healing composition from step (A) with the mammalian cell in the culture medium from step (B).

D. Formulations of the Therapeutic Wound Healing Compositions of Embodiment One (I.A-G)

Once prepared, the inventive therapeutic wound healing compositions of Embodiment One (I.A-G) may be stored for future use or may be formulated in effective amounts with pharmaceutically acceptable carriers to provide a wide variety of pharmaceutical preparations. Examples of pharmaceutically acceptable carriers are pharmaceutical appliances, topical vehicles (non-oral and oral), and ingestible vehicles.

Examples of pharmaceutical appliances are sutures, staples, gauze, bandages, burn dressings, artificial skins, liposome or micell formulations, microcapsules, aqueous vehicles for soaking gauze dressings, and the like, and mixtures thereof. Non-oral topical compositions employ non-oral topical vehicles, such as creams, gels, formulations, foams, ointments and sprays, salves, and films, which are intended to be applied to the skin or body cavity and are not intended to be taken by mouth. Oral topical compositions employ oral vehicles, such as mouthwashes, rinses, oral sprays, suspensions, and dental gels, which are intended to be taken by mouth but are not intended to be ingested. Ingestible compositions employ ingestible or partly ingestible vehicles such as confectionery bulking agents which include hard and soft confectionery such as lozenges, tablets, toffees, nougats, suspensions, chewy candies, and chewing gums.

In one form of the invention, the therapeutic wound healing composition is incorporated into a pharmaceutical appliance which may be in the form of sutures, staples, gauze, bandages, bum dressings, artificial skins, liposome or micell formulations, microcapsules, aqueous vehicles for soaking gauze dressings, and the like, and mixtures thereof. A variety of traditional ingredients may optionally be included in the pharmaceutical composition in effective amounts such as buffers, preservatives, toxicity adjusting agents, antioxidants, polymers for adjusting viscosity or for use as extenders, and excipients, and the like. Specific illustrative examples of such traditional ingredients include acetate and borate buffers, thimerosal, sorbic acid, methyl and propyl paraben and colorobutanol preservatives; sodium chloride and sugars to adjust the toxicity; and excipients such as manitol, lactose and sucrose. Other conventional pharmaceutical additives known to those having ordinary skill in the pharmaceutical arts may also be used in the pharmaceutical composition.

In accordance with this invention, therapeutically effective amounts of the therapeutic wound healing compositions of the present invention may be employed in the pharmaceutical appliance. These amounts are readily determined by those skilled in the art without the need for undue experimentation. The exact amount of therapeutic wound healing composition employed is subject to such factors as the type and concentration of the therapeutic wound healing composition and the type of pharmaceutical appliance employed. Thus, the amount of therapeutic wound healing composition will be varied in order to obtain the result desired in the final product and such variations are within the capabilities of those skilled in the art without need for undue experimentation. In a preferred embodiment, the pharmaceutical composition will comprise the therapeutic wound healing composition in an amount from about 0.1% to about 100%, by weight of the pharmaceutical composition. In a more preferred embodiment, the pharmaceutical composition will comprise the therapeutic wound healing composition in an amount of about 0.1% to about 25%, by weight of the pharmaceutical composition. In a most preferred embodiment, the pharmaceutical composition will comprise the therapeutic wound healing composition in an amount of about 0.1% to about 15%, by weight of the pharmaceutical composition.

The therapeutic wound healing composition may also be delivered by using ionophoresis.

The present invention extends to methods for making the pharmaceutical compositions. In general, a pharmaceutical composition is made by contacting a therapeutically effective amount of a therapeutic wound healing composition with the pharmaceutical appliance and the other ingredients of the final desired pharmaceutical composition. The therapeutic wound healing composition may be absorbed onto a pharmaceutical appliance.

Other ingredients will usually be incorporated into the composition as dictated by the nature of the desired composition as well known by those having ordinary skill in the art. The ultimate pharmaceutical compositions are readily prepared using methods generally known in the pharmaceutical arts.

In another form of the invention, the therapeutic wound healing composition is incorporated into a non-oral topical vehicle which may be in the form of a cream, gel, foam, ointment, spray, and the like. Typical non-toxic non-oral topical vehicles known in the pharmaceutical arts may be used in the present invention. The preferred non-oral topical vehicles are water and pharmaceutically acceptable water-miscible organicsolvents such as ethyl alcohol, isoprophyl alcohol, propylene glycol glycerin, and the like, and the mixtures of these solvents. Water-alcohol mixtures are particularly preferred and are generally employed in a weight ratio from about 1:1 to about 20:1, preferably from about 3:1 to about 20:1, and most preferably from about 3:1 to about 10:1, respectively.

The non-oral topical therapeutic wound healing compositions may also contain conventional additives employed in those products. Conventional additives include humectants, emollients, lubricants, stabilizers, dyes, and perfumes, providing the additives do not interfere with the therapeutic properties of the therapeutic wound healing composition.

The coloring agents (colors, colorants) useful in the non-oral topical therapeutic wound healing composition are used in amounts effective to produce the desired color. These coloring agents include pigments which may be incorporated in amounts up to about 6% by weight of the non-oral topical therapeutic wound healing composition. A preferred pigment, titanium dioxide, may be incorporated in amounts up to about 2%, and preferably less than about 1%, by weight of the non-oral topical therapeutic wound healing composition. The coloring agents may also include natural food colors and dyes suitable for food, drug and cosmetic applications. These coloring agents may also include natural food colors and dyes suitable for food, drug and cosmetic applications. These coloring agents are known as F.D.& C. dyes and lakes. The materials acceptable for the foregoing uses are preferable water-soluble. Illustrative non limiting examples include the indigoid dye known as F.D.& C. Blue No. 2, which is the disodium salt of 5,5-indigotindisulfonic acid. Similarly, the dye known as F.D.& C. Green No 1 comprises a triphenylmenthane dye and is the monosodium salt of 4->4-(N-ethyl-p-sulfoniumbenzylamino) diphenylmenthylene!-1-(N-ethyl-N-p-sulfoniumbenzyl) delta-2,5-cyclohexadien eimine!. A full recitation of all F.D.& C. coloring agents and their corresponding chemical structures may be found in the Kirk-Othmer Encyclopedia of Chemical Technology, 3rd Edition, in volume 5 at pages 857–884, which text is incorporated herein by reference.

In accordance with this invention, therapeutically effective amounts of the therapeutic wound healing compositions of the present invention may be admixed with a non-oral topical vehicle to form a topical therapeutic wound healing composition. These amounts are readily determined by those skilled in the art without the need for undue experimentation. In a preferred embodiment, the non-oral topical therapeutic wound healing compositions will comprise the therapeutic wound healing composition in an amount from about 0.1% to about 10% and a nonoral topical vehicle in a quantity sufficient to bring the total amount of composition to 100%, by weight of the non-oral topical therapeutic wound healing composition. In a more preferred embodiment, the non-oral topical therapeutic would healing compositions will comprise the therapeutic wound healing composition in an amount from about 0.1% to about 5%, and in most preferred embodiment, the non-oral topical therapeutic wound healing compositions will comprise the therapeutic wound healing composition in an amount from about 0.1% to about 2%, and anon-oral topical vehicle in a quantity sufficient to bring the total amount of composition to 100%, by weight of the non-oral topical therapeutic wound healing composition.

The present invention extends to methods for preparing the non-oral topical therapeutic wound healing compositions. In such a method, the non-oral topical therapeutic wound healing composition is prepared by admixing a therapeutically effective amount of the therapeutic wound healing composition of the present invention and a nontopical vehicle. The final compositions are readily prepared using standard methods and apparatus generally known by those skilled in the pharmaceutical arts. The apparatus useful in accordance with the present invention comprises mixing apparatus well known in the pharmaceutical arts, and therefore the selection of the specific apparatus will be apparent to the artisan.

In another form of the invention, the therapeutic wound healing composition is incorporated into an oral topical vehicle which may be in the form of a mouthwash, rinse, oral spray, suspension, dental gel, and the like. Typical nontoxic oral vehicles known in the pharmaceutical arts may be used in the present invention. The preferred oral vehicles are water, ethanol, and water-ethanol mixtures. The waterethanol mixtures are generally employed in a weight ratio from about 1:1 to about 20:1, preferably from about 3:1 to about 20:1, and most preferably from about 3:1 to about 10:1, respectively. The pH value of the oral vehicle is generality from about 4 to about 7, and preferably from about 5 to about 6.5. An oral topical vehicle having a pH value below about 4 is generally irritating to the oral cavity and an oral vehicle having a pH value greater than about 7 generally results in an unpleasant mouth feel.

The oral topical therapeutic wound healing compositions may also contain conventional additives normally employed in those products. Conventional additives include fluorine providing compound, a sweetening agent, a flavoring agent, a coloring agent, a humectant, a buffer, and an emulsifier, providing the additives do not interfere with the therapeutic properties of the therapeutic wound healing composition.

The coloring agents and humectants, and the amounts of these additives to be employed, set out above as useful in the non-oral topical therapeutic wound healing composition may be used in the oral topical therapeutic wound healing composition.

Fluorine providing components may be fully or slightly water soluble and are characterized by their ability to release fluoride ions or fluoride containing ions in water and by their lack or reaction with other components in the composition. Typical fluorine providing compounds are inorganic fluoride salts such as water-soluble alkali metal, and heavy metal salts, for example, sodium fluoride, potassium fluoride, ammonium fluoride, cuprous fluoride, zinc fluoride, stannic fluoride, stannous fluoride, barium fluoride, sodium fluorosilicate, ammonium fluorosilicate, sodium fluorozirconate, sodium monofluorophosphate, aluminum mono-and-difluoride and monofluorophosphates, such as sodium and stannous fluoride, sodium monofluorophospate and mixtures thereof, are preferred.

The amount of fluorine providing compound present in the present oral topical therapeutic wound healing composition is dependent upon the type of fluorine providing compound employed, the solubility of the fluorine compound, and the nature of the final oral therapeutic wound healing composition. The amount of fluorine providing compound used must be a nontoxic amount. In general, the fluorine providing when used will be present in an amount up to about 1%, preferably from about 0.001% to about 0.1%, and most preferably from about 0.001% to about 0.1%, and most preferably from about 0.001% to about 0.05%, by weight of the oral topical therapeutic wound healing composition.

When sweetening agents (sweeteners) are used, those sweeteners well known in the art, including both natural and artificial sweeteners, may be employed. The sweetening agent used may be selected from a wide range of materials including water-soluble sweetening agents, water-soluble artificial sweetening agents, water-soluble sweetening agents derived from naturally occurring water-soluble sweetening agents, dipeptide based sweetening agents, and protein based sweetening agents, including mixtures thereof. Without being limited to particular sweetening agents, representative categories and examples include:

(a) water-soluble sweetening agents such as monosacchardes, disaccharides and polyaccharides such as xylose, ribose, glucose (dextrose), mannosse, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxatahizine-4-one-2-2-dioxide, the potassium salt of 3,4-dihydro-6-methyl-1, 2,3,-oxathizine-4-one-2,2-dioxide (Acesufame-K), the free acid form of saccharin, and the like;

(c) dipeptide based sweeteners, such as L-aspartic acid derived sweeteners, such as L-aspartyl-L-phenylalaunie methyl ester (Aspartame) and materials describes in U.S. Pat. No. 3,492,131, L-Alpha-aspartyl-N-(2,2,4,4-tetamethyl-3-theitanyl)D-alanin-amide hydrate (Altrame), methyl esters of L-aspartyl-L-phenylglycerine and L-aspartyl-L-2-5dihydrophenylglycerine, L-aspartyl-2,5dydro-L-phenylaanine; L-aspartyl-L-(1-cyclohexen)alanine, and the like;

(d) water-soluble sweeteners derived from naturally occurring water-soluble sweeteners, such as chlorinated derivatives or ordinary sugar (sucrose), e.g., chlorodexosugar derivatives such as derivatives of chlorodeoxysucrose or chlorodexoygalactosucrose, known, for example, under the product designation of Sucrose; examples of chlorodexoysucrose and chlorodeoxygalacto-sucrose derivatives include but not limited to: 1-chloro-1'-dexoysucrose; 4-chloro-4-deoxy-Alpha-D-galacto-pyranosyl-Alpha-D-fructofuranoside, or 4-chloro-4-deoxygalactosucrose; 4-chloro-4-deoxy-Alpha-D-galacto-pyroanosyl-1-chloro-1deoxy-.beta.-D-fruct o-furanoside, or 4,1'-dichloro4,1'-dideoxygalactosucrose; 1', 6'-dichloro-1', 6'-dideoxysucrose;4-chloro-4-deoxy-Alpha-D-galacto-pyranosyl-1,6-dichloro-1,6-dideoxy-.beta.-D-fructo-furanoside, or 4,1',6'-trichloro-4,1',6'trideoxygalacto-sucrose; 4,6-dichloro4,6-deoxy-Alpha-D-galacto-pyranosyl-6chloro-6-deoxy-.beta.-D-fructofuranoside, or 4,6,6'-trichloro4,6,6'trideoxygalactosucrose; 6,1',6'-trichloro-6,1',6'-trideoxysucrose; 4,6-dichloro4, 6dideoxy-Alpha-D-galacto-pyranosyl-1,6dichloro-1,6-di-deoxy-.beta,-D-fructofuranoside, or 4,6,1',6'-tetrachloro4,6,1',6'-tetradeoxygalacto-sucrose; and 4,6, 1',6'-tetrachloro-4,6,1',6'-tetradeoxy-sucrose; and (e) protein based sweeteners such as thaumaoccous danielli (Thaumatin I and II).

In general, and effective amount of sweetening agent is utilized to provide the level of sweetness desired in the particular oral topical therapeutic wound healing composition, and this amount will vary with the sweetener selected and the final oral therapeutic product desired. The amount of sweetener normally present is in the range from about 0.0025% to about 90%, by weight of the oral topical therapeutic wound healing composition, depending upon the sweetener used. The exact range of amounts for each type of sweetener is well known in the art and is not the subject of the present invention.

The flavoring agents (flavors, flavorants) which may be used include those flavors known to the skilled artisan, such as natural and artificial flavors. Suitable flavoring agents include mints, such as peppermint, citrus flavors such as orange and lemon, artificial vanilla, cinnamon, various fruit flavors, both individual and mixed, and the like.

The amount of flavoring agent employed in the oral topical therapeutic wound healing composition is normally a matter of preference subject to such factors as the type of final oral therapeutic wound healing composition, the individual flavor employed, and the strength of flavor desired. Thus, the amount of flavoring may be varied in order to obtain the result desired in the final product and such variations are within the capabilities of those skilled in the art without the need for undo experimentation. The flavoring agents, when used, are generally utilized in amounts that may, for example, range in amounts from about 0.05% to about 6%, by weight of the oral topical therapeutic wound healing composition.

Suitable buffer solutions useful in the oral topical therapeutic wound healing compositions include citric acid-sodium citrate solution, phosphoric acid-sodium acetate solution in amounts up to about 1%, and preferably from about 0.05% to about 0.5% by weight of the oral topical therapeutic wound healing composition.

In accordance with this invention, therapeutically effective amounts of the therapeutic wound healing compositions of the present invention may be admixed with an oral topical vehicle to form a topical therapeutic wound healing composition. These amounts are readily determined by those skilled in the art without the need for undue experimentation. In a preferred embodiment, the oral topical therapeutic wound healing compositions will comprise the therapeutic wound healing composition in an amount from about 0.1% to about 10% and a oral topical vehicle in a quantity sufficient to bring the total amount of composition to 100%, by weight of the oral topical therapeutic wound healing composition. In a more preferred embodiment, the oral topical therapeutic wound healing composition in an amount from about 0.1% to about 5%, and in a most preferred embodiment, the oral topical therapeutic wound healing compositions will comprise the therapeutic wound healing composition in an amount from about 0.1% to about 2%, and a oral topical vehicle in quantity sufficient to bring the total amount of composition to 100%, by weight of the oral topical therapeutic wound healing composition.

The present invention extends to methods for preparing the oral topical therapeutic wound healing compositions. In such a method, the oral topical therapeutic wound healing composition is prepared by admixing a therapeutically effective amount of the therapeutic wound healing composition of the present invention and an oral topical vehicle. The final compositions are readily prepared using standard methods and apparatus generally known by those skilled in the pharmaceutical arts. The apparatus useful in accordance with the present invention comprises mixing apparatus well known in the pharmaceutical arts, and therefore the selection of the specific apparatus will be apparent to the artisan.

In a preferred embodiment, an oral topical therapeutic wound healing composition is made by first dissolving coloring agents, sweetening agents, and similar additives in water. The therapeutic wound healing composition is then admixed with the aqueous solution. Then sufficient water or ethanol, or mixtures of water and ethanol, are added to the solution with mixing until the final solution volume is reached. In a more preferred embodiment, the therapeutic wound healing composition is added to the solution as the final ingredient. The final oral topical therapeutic wound healing compositions are readily prepared using methods generally known in the pharmaceutical arts.

The oral therapeutic wound healing composition may also be in the form of dental gel. As used herein, the term "gel" means a solid or semisolid colloid which contains considerable quantities of water. The colloid particles in a gel are linked together in a coherent meshwork which immobilizes the water contained inside the meshwork.

The dental gel compositions of the present invention contain the conventional additives set out above for oral topical therapeutic wound healing compositions such as mouthwashes, rinses, oral sprays, and suspension and in addition, may contain additional additives such as a polishing agent, a desensitizing agent, and the like, providing the additional additives do not interfere with the therapeutic properties of the therapeutic wound healing composition.

In a dental gel composition, the oral vehicle generally comprises water, typically in an amount from about 10% to about 90%, by weight of the dental gel composition. Polyethylene glycol, propylene glycol, glycerin, and mixtures thereof may also be present in the vehicle as humectants or binders in amounts from about 18% to about 30%, by weight of the dental gel composition. Particularly preferred oral vehicles comprise mixtures of water with polyethylene glycol or water with glycerin and polypropylene glycol.

The dental gels of the present invention include a gelling agent (thickening agent) such as a natural or synthetic gum or gelatin. Gelling agents such as hydroxyethyl cellulose, methyl cellulose, glycerin, carboxypolymethylene, and gelatin and the like, and mixtures thereof may be used. The preferred gelling agent is hydroxyethyl cellulose. Gelling agents may be used in amounts from about 0.5% to about 5%, and preferably from about 0.5% to about 2%, by weight of the dental gel composition.

The dental gel compositions of the present invention may also include a polishing agent. In clear gels, a polishing agent of colloidal silica and/or alkali metal aluminosilicate complexes is preferred since these materials have refractive indices close to the refractive indices of the gelling systems commonly used in dental gels. In non-clear gels, a polishing agent of calcium carbonate or calcium dihydrate may be used. These polishing agents may be used in amounts up to about 75%, and preferably in amounts up to about 50%, by weight of the dental gel composition.

The dental gel may also contain a desensitizing agent such as a combination of citric acid and sodium citrate. Citric acid may be used in an amount from about 0.1% to about 3%, and preferably from about 0.2% to about 9%, and preferably from about 0.6% to about 3%, by weight of the dental gel composition.

In accordance with this invention, therapeutically effective amounts of the therapeutic wound healing compositions of the present invention may be admixed into the dental gel compositions. These amounts are readily determined by those skilled in the art without the need for undue experimentation. In a preferred embodiment, the dental gel compositions will comprise the therapeutic wound healing composition in an amount from about 0.1% to about 10% and an oral topical vehicle in a quantity sufficient to bring the total amount of composition to 100%, by weight of the dental gel composition. In a more preferred embodiment, the dental gel compositions will comprise the therapeutic wound healing composition in an amount from abut 0.1% to about 5%, and in most preferred embodiment, the dental gel compositions will comprise the therapeutic wound healing dental gel compositions in an amount from about 0.1% to about 2%, and an oral topical vehicle in a quantity sufficient to bring the total amount of composition to 100%, by weight of the dental gel composition.

The present invention extends to methods for preparing the therapeutic dental gel compositions. In such a method, the dental gel composition is prepared by admixing a therapeutically effective amount of the therapeutic wound healing composition of the present invention and an oral topical vehicle. The final compositions are readily prepared using methods generally known by those skilled in the dental and pharmaceutical arts. The apparatus useful in accordance with the present invention comprises mixing apparatus well known in the pharmaceutical arts, and therefore the selection of the specific apparatus will be apparent to the artisan.

In a preferred embodiment, a therapeutic dental gel composition is made by first dispersing a gelling agent in a humectant or water, or a mixture of both, the admixing to the dispersion an aqueous solution of the water-soluble additives such as the fluorine providing compound, sweeteners and the like, then adding the polishing agent, and lastly admixing the flavoring agent and the therapeutic wound healing composition. The final gel mixture is then tubed or otherwise packaged. The liquids and solids in a gel product are proportioned to form a creamy or gelled mass which is extrudable from a pressurized container or from a collapsible tube. The final therapeutic wound healing compositions are readily prepared using methods generally known in the pkarmaceutical arts.

In yet another form of the invention, the therapeutic wound healing composition is incorporated into an ingestible vehicle. The ingestible vehicle may be confectionery bulking agent in the form of lozenges, tablets, toffees, nougats, suspensions, chewy candies, chewing gums, and the like. The pharmaceutically acceptable carriers may be prepared from a wide range of materials including, but not limited to, diluents, binders and adhesives, lubricants, disintegrants, coloring agents, bulking agents, flavoring agents, sweetening agents and miscellaneous materials such as buffers and absorbents that may be needed in order to prepare a particular therapeutic confection.

The preparation of confectionery formulation is historically well known and has changes little through the years. Confectionery items have been classified as either "hard" confectionery or "soft" confectionery. The therapeutic wound healing compositions of the present invention can be incorporated into confectionery compositions by admixing the inventive composition into conventional hard and soft confections.

As used herein, the term confectionery material means a product containing a bulking agent selected from a wide variety of materials such as sugar, corn syrup, and in the case of sugarless bulling agents, sugar alcohols such as sorbitol and mannitol and mixtures thereof. Confectionery material may include such exemplary substances as lozenges, tablets, toffee, nougat, suspensions, chewy candy, chewing gum and the like. The bulking agent is present in a quantity sufficient to bring the total amount of composition to 100%. In general, the bulking agent will be present in amounts up to about 99.98%, preferably in amounts up to about 99.9%, and more preferably in amounts up to about 99%, by weight of the ingestible therapeutic wound healing composition.

Lozenges are flavored medicated dosages forms intended to be sucked and held in the mouth. Lozenges may be in the form of various shapes such as flat, circular, octagonal and biconvex forms. The lozenge bases are generally in two forms: hard boiled candy and compressed tablet lozenges.

Hard boiled candy lozenges may be processed and formulated by conventional means. In general, a hard boiled candy lozenge has a base composed of a mixture of sugar and other carbohydrate bulking agents kept in an amorphous or glassy condition. This amorphous or glassy form is considered a solid syrup of sugar generally having from about 0.5% to about 1.5% moisture. Such materials normally contain up to about 92% corn syrup, up to about 55% sugar and from about 0.1% to about 5% water, by weight of the final composition. The syrup component is generally prepared from corn syrups high in fructose, but may include other materials. Further ingredients such as flavoring agents, sweetening agents, acidulants, coloring agents and the like may also be added.

Boiled candy lozenges may also be prepared from non-fermentable sugars such as sorbitol, mannitol, and hydrogenated corn syrup. Typical hydrogenated corn syrups are Lycasin, a commercially available product manufactured by Roquette Corporation, and Hystar, a commercially available product manufactured by Lonza, Inc. The candy lozenges may contain up to about 95% sorbitol, a mixture of sorbitol and mannitol in a ratio from about 9.5:0.5 up to about 7.5:2.5, and hydrogenated corn syrup up to about 55%, by weight of the solid syrup component.

Boiled candy lozenges may be routinely prepared by conventional methods such as those involving fire cookers, vacuum cookers, and scraped-surface cookers also referred to as high speed atmospheric cookers.

Fire cookers involve the traditional method of making a boiled candy lozenge base. In this method, the desired quantity of carbohydrate bulking agent is dissolved in water by heating the agent in kettle until the bulking agent dissolves. Additional bulking agent may be added and cooking continued until a final temperature of 145. degree. C. to 156. degree. C. is achieved. The batch is then cooled and worked as a plastic-like mass to incorporate additives such as flavors, colorants and the like.

A high-speed atmospheric cooker uses a heat-exchanger surface which involves spreading a film of candy on a heat exchange surface, the candy is heated to 165.degree. C. to 170.degree. C. in a few minutes. The candy is then rapidly cooled to 100.degree. C. to 120degree. C. and worked as a plastic-like mass enabling incorporation of the additives, such as flavors, colorants and the like.

In vacuum cookers, the carbohydrate bulking agent is boiled to 125.degree. C. to 132.degree. C., vacuum is applied and additional water is boiled off without extra heating. When cooking is complete, the mass is a semi-solid and has a plastic-like consistency. At this point, flavors, colorants, and other additives are admixed in the mass by routine mechanical mixing operations.

The optimum mixing required to uniformly mix the flavoring agents, coloring agents and other additives during conventional manufacturing of boiled candy lozenges is determined by the time needed to obtain a uniform distribution of the materials. Normally, mixing times of from 4 to 10 minutes have been found to be acceptable.

Once the boiled candy lozenge has been properly tempered, it may be cut into workable portions or formed into desired shapes. A variety of forming techniques may be utilized depending upon the shape and size of the final product desired. A general discussion of the composition and preparation of hard confections may be found in H. A. Liberian, Pharmaceutical Dosage Forms: Tablets, Volume 1 (1980), Marvel Decker, Inc., New York, N.Y. at pages 339 to 469, which disclosure is incorporated herein by reference.

The apparatus useful in with the present invention comprises cooking and mixing apparatus well known in the confectionery manufacturing arts, and therefore the selection of the specific apparatus will be apparent to the artisan.

In contrast, compressed tablet confections contain particulate materials and are formed into structured under pressure. These confections generally contain sugars in amounts up to about 95%, by weight of the composition, and typical tablet excipients such as binders and lubricants as well as flavoring agents, coloring agents and the like.

In addition to hard confectionery materials, the lozenges of the present invention may be made of soft confectionery materials such as those contained in nougat. The preparation of soft confections, such as nougat, involves conventional methods, such as the combination of two primary components, namely (1) high boiling syrup such as a corn syrup, hydrogenated starch hydorlysate or the like, and (2) a relatively light textured frappe, generally prepared from egg albumin, gelatin, vegetable proteins, such as soy derived compounds, sugarless milk derived compounds such as milk proteins, and mixtures thereof. The frappe is generally relatively light, and may, for example, range in density from about 0.5 to about 0.7 grams/cc.

The high boiling syrup, or "bob syrup" of the soft confectionery is relatively viscous and has a higher density that the frappe component, and frequently contains a substantial amount of carbohydrate bulking agent such as a hydrogenated starch hydrolysate. Conventionally, the final nougat composition is prepared by the addition of the "bob syrup" to the frappe under agitation, to form the basic nougat mixture. Further ingredients such as flavoring agents, additional carbohydrate bulling agent, coloring agents, preservatives, medicaments, mixtures thereof and the like may be added thereafter also under agitation. A general discussion of the composition and preparation of nougat confections may be found in B. W. Minifie, Chocolate, Cocoa and Confectionery; Science and Technology, 2nd edition, AVI Publishing Co., Inc., Westport, Conn. (1980), at pages 424–425, which disclosure is incorporated herein by reference.

The procedure for preparing the soft confectionery involves known procedures. In general, the frappe component is prepared first and thereafter the syrup component is slowly added under agitation at the temperature of at least about 65.degree. C., and preferably at least about 100.degree C. The mixture of components is continued to be mixed to form a uniform mixture, after which the mixture is cooled to a temperature below 80.degree. C., at which point, the flavoring agent may be added. The mixture is further mixed for an additional period until it is ready to be removed and formed into suitable confectionery shapes.

The ingestible therapeutic wound healing compositions may also be in the form of a pharmaceutical suspension. Pharmaceutical suspensions of this invention may be prepared by conventional methods long established in the art of pharmaceutical compounding. Suspensions may contain adjunct materials employed in formulating the suspensions of the art. The suspensions of the present invention can comprise:

(a) preservatives such as butylated hydroyanisole (BHA), butylated hydroxytoluene (BHr), benzoic acid, ascorbic acid, methyl paraben, propyl paraben, tocopherols, and the like, and mixtures thereof. Preservatives are generally present in amounts up to about 1%, and preferably from about 0.05% to about 0.5%, by weight of the suspension;

(b) buffers such as citric acid-sodium citrate, phosphoric acid-sodium phosphate, and acetic acid-sodium acetate in amounts up to about 1%, and preferably from about 0.05% to about 0.5%, by weight of the suspension;

(c) suspending agents or thickeners such as cellulosics like methylcellulose, carregeenans like alginic acid and its derivatives, xanthan gums, gelatin, acacias, and microcrystalline cellulose in amounts up to about 20%, and preferably from about 1% to about 15%, by weight of the suspension;

(d) antifoaming agents such as dimethyl polysiloxane in amounts up to about 0.2%, and preferably from about 0.01% to about 0.1%, by weight of the suspension;

(e) sweetening agents such as those sweeteners well known in the art, including both natural and artificial sweeteners. Sweetening agents such as monosaccharides, disaccharides and polyaccharides such as xylose, ribose, glucose (dextrose), mannose, galactoser, fructose Oevulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof may be utilized in amounts up to about 60%, and preferably from about 20% to about 50%, by weight of the suspension. Water-soluble artificial sweeteners such as soluble saccharin salts, i.e., sodium or calcium saccharin oxathiazine4-one-2-2-dioxide, the potassium salt of 3,4-dihydro-6-methyl-1, 2,3-oxathiazine-4-one-2,2-ioxide (Acesulfame-K), the free acid form of saccharin, and the like may be utilized in amounts from about 0.001 to about 5%, by weight of the suspension;

(f) flavoring agents such as those flavors well known to the skilled artisan, such as natural and artificial flavors and mints, such as peppermint, menthol, citrus flavors such as orange and lemon, artificial vanilla, cinnamon, various fruit flavors, both individual and mixed and the like may be utilized in amounts from about 0.5% to about 5%, by weight of the suspension;

(g) coloring agents such as pigments which may be incorporated in amounts up to about 6%, by weight of the suspension. A preferred pigment, titanium dioxide, may be incorporated in amounts up to about 2%, and preferably less than about 1%, by weight of the suspension. The coloring agents may also include natural food colors and dyes suitable for food, drug and cosmetic applications. These colorants are knows as F.D.& C. dyes and lakes. The materials acceptable for the foregoing uses are preferably water-soluble. Such dyes are generally present in amounts up to about 0.25%, and preferably from about 0.05% to about 0.2%, by weight of the suspension;

(h) decolorizing agents such as sodium metabisulfite, ascorbic acid and the like may be incorporated into the suspension to prevent color changes due to aging. In general, decolorizing agents may be used in amounts up to about 0.25%, and preferably from about 0.05% to about 0.2%, by weight of the suspension; and (i) solubilizers such as alcohol, propylene glycol, polyethylene glycol, and the like may be used to solubilize the flavoring agents. In general, solubilizing agents may be used in amounts up to about 10% and preferably from about 2% to about 5%, by weight of the suspension.

The pharmaceutical suspensions of the present invention may be prepared as follows:

(A) admix the thickener with water heated from about 40° C. to about 95° C., preferably from about 40° C. to about 70° C., to form a dispersion if the thickener is not water soluble or a solution if the thickener is water soluble;

(B) admix the sweetening agent with water to form a solution;

(C) admix the therapeutic wound healing composition with the thickener-water admixture to form a uniform thickener-therapeutic wound healing composition;

(D) combine the sweetener solution with the thickener-therapeutic wound healing composition and mix until uniform; and (E) admix the optional adjunct materials such as coloring agents, flavoring agents, decolorants, solubilizers, antifoaming agents, buffers and additional water with the mixture of step (D) to form the suspension.

The ingestible therapeutic wound healing compositions of this invention may also be in chewable form to achieve acceptable stability and quality as well as good taste and mouth feel in a chewable formulation several considerations are important. These considerations include the amount of active substance per tablet, the flavoring agent employed, the degree of compressibility of the tablet and the organoleptic properties of the composition.

Chewable therapeutic candy is prepared by procedures similar to those used to make soft confectionery. In a typical procedure, a boiled sugar-corn syrup blend is formed to which is added a frappe mixture. The boiled sugar-corn syrup blend may be prepared from sugar and corn syrup blended in parts by weight ration of about 90:10 to about 10:90. The sugar-corn syrup blend is heated to temperatures above about 120.degree. C. to remove water and to form a molten mass. The frappe is generally prepared from gelatin, egg albumin, milk proteins such as casein, and vegetable proteins such as soy protein, and the like, which is added to a gelatin solution and rapidly mixed at ambient temperature to form an aerated sponge like mass. The frappe is then added to the molten candy mass and mixed until homogeneous at temperatures between about 65.degree. C. and about 120.degree. C.

The ingestible therapeutic wound healing composition of the instant invention can then be added to the homogeneous mixture as the temperature is lowered to about 65.degree. C.–95.degree.C. whereupon additional ingredients can then be added such as flavoring agents and coloring agents. The formulation is further cooled and formed into pieces of desired dimensions.

A general discussion of the lozenge and chewable tablet forms of confectionery may be found in H. A. Lieberman and L. Lachmaan, Pharmaceutical Dosage Forms: Tablets Volume 1, Marcel Dekker, Inc. New York, N.Y. at pages 289 to 466, which disclosure is incorporated herein by reference.

In accordance with this invention, therapeutically effective amounts of the therapeutic wound healing compositions of the present invention may be admixed into the hard and soft confectionery products. These amounts are readily determined by those skilled in the art without the need for undue experimentation. In a preferred embodiment, the ingestible therapeutic wound healing composition will comprise the therapeutic wound healing composition in an amount from about 0.01% to about 10%, and an ingestible vehicle, that is a pharmaceutically acceptable carrier, in a quantity sufficient to bring the total amount of composition to 100%, by weight the ingestible therapeutic wound healing composition. In a more preferred composition will comprise the therapeutic wound healing composition in an amount from about 0.1% to about %5, and in a most preferred embodiment, the ingestible composition will comprise the therapeutic wound healing composition in an amount from about 0.01% to about 2%, and an ingestible vehicle in a quantity sufficient to bring the total amount of composition to 100%, by weight the ingestible therapeutic wound healing composition.

The present invention extends to methods of making the ingestible therapeutic wound healing compositions. In such methods, an ingestible therapeutic wound healing composition is prepared by admixing a therapeutically effective amount of the therapeutic wound healing composition with a pharmaceutically-acceptable carrier. The apparatus useful in accordance with the present invention comprises mixing and heating apparatus well known in the confectionery arts, and therefore the selection of the specific apparatus will be apparent to the artisan. The final ingestible therapeutic wound healing compositions are readily prepared using methods generally known in the confectionery arts.

The therapeutic wound healing compositions may also be incorporated into chewing gums. In this form of the invention, the chewing gum composition contains a gum base, a bulking agent, the inventive therapeutic wound healing composition, and various additives.

The gum base employed will vary greatly depending upon various factors such as the type of base desired, the consistency of gum desired and the other components used in the composition to make the final chewing gum product. The gum base may be any water-insoluble gum base known in the art, and includes those gum bases utilized for chewing gums and bubble gums. Illustrative examples of suitable polymers in gum bases include both natural and synthetic elastomers and rubbers. For example, those such as chicle, crown gum, nispero, rosadinha, jelutong, perillo, niger gutta, tunu, balatsa, gutta-ercha, lechi-capsi, sorva, gutta kay, mixtures thereof and the like. Synthetic elastomers such as butadiene-styrene copolymers, ployisobutylene, isobutylene-isoprene copolymers, polyethylene, mixtures thereof and the like are particularly useful.

The gum base may include a nontoxic vinyl polymer, such as polyvinyl acetate and its partial hydrolysate, polyvinyl alcohol, and mixtures thereof. When utilized, the molecular weight of the vinyl polymer may range from about 2,000 up to and including about 94,000.

The amount of gum base employed will vary greatly depending upon various factors such as the type of base used, the consistency of the gum desired and the other components used in the composition to make the final chewing gum product. In general, the gum base will be present in amounts from about 5% to about 94%, by weight of the final chewing gum composition, and preferably in amounts from about 15% to about 45%, and more preferably in amounts from about 15% to abut 35%, and most preferably in amounts from about 20% to about 30%, by weight of the final chewing gum composition.

The gum base composition may contain conventional elastomer solvents to aid in softening the elastomer base component. Such elastomer solvents may comprise terpinene resins such as polymers of Alpha-pinene or .beta.-pinene, methyl, glycerol or pentaerythritol esters of rosins or modified rosins and gums, such as hydrogenated, dinierized or polymerized rosins or mixtures thereof. Examples of elastomers solvents suitable for use herein include the pentaerythritol ester of partially hydrogenated wood or gum rosin, the pentaerydiritol ester of wood or gum rosin, the glycerol ester of polymerized wood rosin, the glycerol ester of partially dimerized wood or gum rosin, the glycerol ester of tall oil rosin, the glycerol ester of wood or gum rosin and the partially hydrogenated wood or gum rosin and the partially hydrogenated methyl ester of wood or rosin, mixtures thereof, and the like. The elastomer solvent may be employed in amounts from about 5% to about 75%, by weight of the gum base, and preferably from about 45% to about 70%, by weight of the gum base.

A variety of traditional ingredients may be included in the gum base in effective amounts such as plasticizers or softeners such as lanolin, palmitic acid, oleic acid, stearic acid, sodium stearate, potassium stearate, glyceryl triacetate, glyceryl lecithin, glyceryl monostearate, polylene glycol monostearatc, acetylated monoglyceride, glycerine, mixture thereof, and the like may also be incorporated into the gum base to obtain a variety of desirable textures and consistency properties. Waxes, for example, natural and synthetic waxes, hydrogenated vegetable oils, petroleum waxes such as polyurethane waxes, polyethylene waxes, paraffin waxes, microcrystallin waxes, fatty waxes, sorbitan monostearate, tallow, propylene glycol, mixtures thereof, and the like may also be incorporated into the gum base to obtain a variety of desirable textures and consistency properties. These traditional additional materials are generally employed in amounts up to about 30%, by weight of the gum base, and preferably in amounts from about 3% to about 20%, by weight of the gum base.

The gum base may include effective amounts of mineral adjuvants such as calcium carbonate, magnesium carbonate, alumina, aluminum hydroxide, aluminum silicate, talc, tricalcium phosphate, dicalcium phosphate and the like as well as mixtures thereof. These mineral adjuvants may serve as fillers and textaral agents. These fillers or adjuvants may be used in the gum base in various amounts. Preferably the amount of filler when used will be present in an amount up to about 60%, by weight of the chewing gum base.

The chewing gum base may additionally include the conventional additives of coloring agents, antioxidants, preservatives and the like. For example, titanium dioxide and other dyes suitable for food, drug and cosmetic applications, known as F.D. & C.dyes, may be utilized. An antioxidant such as butylated hydroxytoluene (BHT), butylated hydroxyanisole (BHA), propyl gallate, and mixtures thereof, may also be included. Other conventional chewing gum additives known to one having ordinary skill in the chewing gum are may also be used in the chewing gum base.

The gum composition may include effective amounts of conventional additives selected from the group consisting of sweetening agents (sweeteners), plasticizers, softeners, emulsifiers, waxes, fillers, bulking agents, mineral adjuvants, flavoring agents (flavors, flavorings), coloring agents (colorants, colorings), antioxidants, acidulants, thickeners, mixtures thereof and the like. Some of these additives may serve more than one purpose. For example, in sugarless gum compositions, the sweetener, e.g., sorbitol other sugar alcohol or mixture thereof, may also function as a bulking agent. Similarly, in sugar containing gum compositions, the sugar sweetener can also function as a bulking agent.

The plasticizers, softeners, mineral adjuvants, colorants, waxes and antioxidants discussed above as being suitable for use in the gum base may also be used in the gum composition. Examples of other conventional additives which may be used include emulsifiers, such as lecithin and glyceryl monostearate, thickeners, used alone or in combination with other softeners, such as methyl cellulose, alginates, carrageenan, xanthan gum, gelatin, carob, tragacanth, locust bean, and carboxy methyl, cellulose, acidulants such as malic acid, adipic acid, citric acid, tartaric acid, fumaric acid, and mixtures thereof, and fillers, such as those discussed about under the category of mineral adjuvants. The fillers when used may be utilized in an amount up to about 60%, by weight of the gum composition.

Bulking agents (carriers, extenders) suitable for use in chewing gums include sweetening agents selected from the group consisting of monosaccharides, disaccharides, polysaccharides, sugar alcohols, and mixtures thereof, polydextrose; maltodextrins; miners, such as calcium carbonate, talc, titanium dioxide, dicalcium phosphate, and the like. Bulking agents may be used in amounts up to about 90%, by weight of the final gum composition, with amounts from about 40% to about 70%,by weight of the gum composition being preferred, with from about 50% to about 65%, by weight, being more preferred and from about 55% to about 60%, by weight of the chewing gum composition, being most preferred.

The sweetening agent used may be selected from a wide range of materials including water-soluble sweeteners, water-soluble artificial sweeteners, water-soluble sweeteners derived from naturally occurring water-soluble sweeteners, dipeptide based sweeteners, and protein based sweeteners, including mixtures thereof. Without being limited to particular sweeteners, representative categories and examples include:

(a) water-soluble sweetening agents such as monosaccharides, disaccharides and polysaccharides such as xylose, ribulose, glucose (dextrose), mannose, galactose, fructose (evulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4one-2,2-dioxide, the potassium salt of 3,4-dihydro-6-methyl-1, 2,3-oxythiazine-4-one-2,2-ioxide (Acesulfame-K), the free acid form of saccharin, and the like;

(c) dipeptide based sweeteners, such as L-aspartic acid derived sweeteners, such as L-aspartyl-L-phenylalanine methyl ester (Aspartame) and the materials described in U.S. Pat. No. 3,492,131, L-Alpha-aspartyl-N-(22,2,4,4-tetramethyl-3-thietanyl)-D-alanin-amide hydrate (Alitame), methyl esters of -aspartyl-L-phenylglycerine and L-aspartyl-L-(1-cyclohexen)-alanine, and the like;

(d) water-soluble sweeteners derived from naturally occurring water-soluble sweeteners, such as chlorinated derivatives or ordinary sugar (sucrose), known, for example, under the product designation of Sucralose; and (e) protein based sweeteners such as thaumaoccous danielli (Thaumatin I and II).

In general, an effective amount of sweetener is utilized to provide the level of bulk and/or sweetness desired, and this amount will vary with the sweetener selected. This amount of sweetener will normally be present in amounts from about 0.0025% to about 90%, by weight of the gum composition, depending upon the sweetener used. The exact range of amounts for each type of sweetener is well known in the art and is not the subject of the present invention. The amount of sweetener ordinarily necessary to achieve the desired level of sweetness is independent from the flavor level achieved from flavor oils.

Preferred sugar based-sweeteners are sugar (sucrose), corn syrup and mixtures thereof. Preferred sugarless sweeteners are the sugar alcohols, artificial sweeteners, dipeptide based sweeteners and mixtures thereof. Preferably, sugar alcohols are used in the sugarless compositions because these sweeteners can by used in amounts which are sufficient to provide bulk as well as the desired level of sweetness. Preferred sugar alcohols are selected from the group consisting of sorbitol, xylitol, maltitol, mannitol, and mixtures thereof. More preferably, sorbitol or a mixture of sorbitol and mannitol is utilized. The gamma form of sorbitol is preferred. an artificial sweetener or dipeptide based sweetener is preferably added to the gum compositions which contain sugar alcohols.

The coloring agents useful in the gum compositions are used in amounts effective to produce the desired color. These coloring agents include pigments which may be incorporated in amounts up to about 6% by weight of the gum composition. A preferred pigment, titanium dioxide, may be incorporated in amounts up to about 2%, and preferably less than about 1% by weight of the composition. The colorants may also include natural food colors and dyes suitable for food, drug and cosmetic applications. These colorants are known as F.D. & C. dyes and lakes. The materials acceptable for the foregoing uses are preferably water-soluble. Illustrative nonlimiting examples include the indigoid dye known as F.D.& C. Blue No. 2, which is the disodium salt of 5,5 indigotidisulfonic acid. Similarly, the dye known as F.D.& C. Green No. 1 comprises a triphenylmethane dye and is the monosodium salt of 4->4-(N-ethyl-p-sulfoniumbenzylamino)diphenylmethylene!->1-(N-ethyl-N-p-sulfomumbenzyl)-delta-2,5cyclohexadieneimine!. A full recitation of all F.D.& C. colorants and their corresponding chemical structures may be found in the Kirk-Othmer Encyclopedia of Chemical Technology, 3rd Edition, in volume 5 at pages 857–884, which text is incorporated herein by reference.

Suitable oils and fats usable in gum compositions include partially hydrogenated vegetable or animal fats, such as coconut oil, palm kernel oil, beef tallow, lard, and the like. These ingredients when used are generally present in amounts up to about 7%, by weight, and preferably up to about 3.5%, by weight of the gum composition.

In accordance with this invention, therapeutically effective amounts of the therapeutic wound healing compositions of the present invention may be admixed into a chewing gum. These amounts are readily determined by those skilled in the art without the need for undue experimentation. In a preferred embodiment, the final chewing gum composition will comprise the therapeutic wound healing composition in an amount from about 0.1% to about 10% and a chewing gum composition in a quantity sufficient to bring the total amount of composition to 100%, by weight of the chewing gum composition. In a more preferred embodiment, the final chewing gum composition will comprise the therapeutic wound healing composition in an amount from about 0.1% to about 5%, and in a most preferred embodiment, the final chewing gum composition will comprise the therapeutic wound healing composition in an amount from about 0.1% to about 2%, and a chewing gum composition in a quantity sufficient to bring the total amount of composition to 100%, by weight of the chewing gum composition.

The present invention extends to methods of making the therapeutic chewing gum compositions, the therapeutic wound healing compositions may be incorporated into an otherwise conventional chewing gum composition using standard techniques and equipment known to those skilled in the art. The apparatus useful in accordance with the present invention comprises mixing and heating apparatus well known in the chewing gum manufacturing arts, and therefore the selection of the specific apparatus will be apparent to the artisan.

For example, a gum base is heated to a temperature sufficiently high enough to soften the base without adversely effecting the physical and chemical make up of the base. The optimum temperatures utilized may vary depending upon the composition of the gum base used, but such temperatures are readily determined by those skilled in the art without undue experimentation.

The gum base is conventionally melted at temperatures that range from about 60° C. to about 120° C. For a period of time sufficient to render the base molten. For example, the gum base may be heated under these conditions for a period of about thirty minutes just prior to being admired incrementally with the remaining ingredients of the base such as the plasticizer, fillers, the bulking agent and/or sweeteners, the softener and coloring agents to plasticize the blend as well as to modulate the hardness, viscoelasticity and formability of the base. The chewing gum base is then blended with the therapeutic wound healing composition of the present invention which may have been previously blended with other traditional ingredients. Thereafter the gum composition mixture may be formed into desirable chewing gum shapes.

In a specific embodiment, the invention is directed to a therapeutic pharmaceutical composition for preventing and reducing injury to mammalian cells, and increasing the resuscitation rate of injured mammalian cells, which comprises:

A) a therapeutically effective amount of a therapeutic wound healing composition of Embodiment One (I.A-G) selected from the group consisting of:
(IA.)
(a) zinc oxide; and
(b) all forms and precursors of Vitamins A; and,
(c) all forms and precursors of Vitamin D.
(I.B)
(a) zinc oxide; and
(b) all forms and precursors of Vitamin A; and
(c) all forms and precursors of Vitamin D;
(d) all forms and precursors of Vitamin E.
(I.C)
(a) zinc oxide; and
(b) all forms and precursors of Vitamin A; and
(c) all forms and precursors of Vitamin D; and
(d) all forms and precursors of Vitamin K.
(I.D)
(a) zinc oxide; and
(b) all forms and precursors of Vitamin A; and
(c) all forms and precursors of Vitamin D; and
(d) all forms and precursors of Vitamin E; and
(e) all forms and precursors of Vitamin K.
(I.E)
(a) all forms and precursors of Vitamin A; and
(b) all forms and precursors of Vitamin D; and
(c) all forms and precursors of Vitamin E.
(I.F)
(a) all forms and precursors of Vitamin A; and
(b) all forms and precursors of Vitamin D; and
(c) all forms and precursors of Vitamin E; and
(d) all forms and precursors of Vitamin K.
(I.G)
(a) all forms and precursors of Vitamin A; and
(b) all forms and precursor of Vitamin D; and
(c) all forms and precursors of Vitamin K; and
(B) a pharmaceuticaly acceptable carrier.

The pharmaceutically acceptable carrier may be selected for the group consisting of pharmaceutical appliance, topical vehicles, and ingestible vehicles.

In another specific specific embodiment, the invention is directed to a method of preparing a therapeutic pharmaceutical composition for preventing and reducing injury to mammalian cells, and increasing the resuscitation of injured mammalian cells, which comprise the steps of:

(A) providing a therapeutically effective amount of a therapeutic wound healing composition of Embodiment One (I.A-G) selected from the group consisting of:
(IA.)
(a) zinc oxide; and
(b) all forms and precursors of Vitamins A; and,
(c) all forms and precursors of Vitamin D.
(I.B)
(a) zinc oxide; and
(b) all forms and precursors of Vitamin A; and
(c) all forms and precursors of Vitamin D;
(d) all forms and precursors of Vitamin E.
(I.C)
(a) zinc oxide; and
(b) all forms and precursors of Vitamin A; and
(c) all forms and precursors of Vitamin D; and
(d) all forms and precursors of Vitamin K.
(I.D)
(a) zinc oxide; and
(b) all forms and precursors of Vitamin A; and
(c) all forms and precursors of Vitamin D; and
(d) all forms and precursors of Vitamin E; and
(e) all forms and precursors of Vitamin K.
(I.E)
(a) all forms and precursors of Vitamin A; and
(b) all forms and precursors of Vitamin D; and
(c) all forms and precursors of Vitamin E.
(I.F)
(a) all forms and precursors of Vitamin A; and
(b) all forms and precursors of Vitamin D; and
(c) all forms and precursors of Vitamin E; and
(d) all forms and precursors of Vitamin K.
(I.G)
(a) all forms and precursors of Vitamin A; and
(b) all forms and precursor of Vitamin D; and
(c) all forms and precursors of Vitamin K; and
(B) finding a pharmaceutically acceptable carrier, and
(C) admixing the therapeutic wound healing composition from step (A) and the pharmaceutically acceptable carrier from step (B) to form a therapeutic pharmaceutical composition.

The invention is further illustrated by examples which are not intended to limit the effective scope of the claims.

II. Antibacterial-wound Healing Compositions

A. Embodiment Two (I.A-G+X+Y)

Applicant has discovered therapeutic antibacterial-wound healing compositions (I.A-G+X+Y) which comprise an antibacterial agent (X), and an antifungal agent, and the wound healing compositions of Embodiment One (I.A-G+X+Y) Preferably, the wound healing composition (I.A) comprises (a) zinc oxide and b) two or more fat soluble vitamins. Antibacterial agents can treat bacterial infections in a patient but do not promote the wound healing process. It is the same with antifungal agents. Wound healing compositions can increase the resuscitation rate of injured mammalian cells and the proliferation rate of new mammalian cells to replace dead cells but do not reduce virus titers. The applicant has found that the combination of an antibacterial and/or antifungal agent and a wound healing composition results in a therapeutic antibacterial/antifungal-wound healing composition which reduces the size, duration, and severity of infected wounds.

The combination of the antibacterial agent, and/or the antifungal agent, and the wound healing compositions of the present invention provides a pharmaceutical composition useful for treating infected wounds and having an enhanced ability to prevent and reduce injury to mammalian cells and further increase the resuscitation rate of injured mammalian cells. The tissue damage associated with many bacterial diseases is believed to be caused by the production of cellular produced active oxygen species. Combination of the antibacterial agent and the wound heating compositions may suppress such reactive oxygen-linked tissue injury.

The antibacterial agents which may be employed in the antibacterial-wound healing therapeutic compositions may be selected from a wide variety of water-soluble and water-insoluble drugs and their acid addition or metallic salts. Both organic and inorganic salts may be used provided the antibacterial agent maintains its medicament value. The antibacterial agents may be selected from a wide range of therapeutic agents and mixtures of therapeutic agents which may be administered in sustained release or prolonged action form. Nonlimiting illustrative specific examples of antibacterial agents include bismuth containing compounds, sulfonamides; nitrofurans, metronidazole, tinidazole, nimorazole, benzoic acid; aminoglycosides, macrolides, penicillins, polypeptides, tetracyclines, cephalosporins, chloramphenicol, and clindamycin. Preferably, the antibacterial agent is selected from the group consisting of bismuth containing compounds, such as, without limitation, bismuth aluminate, bismuth subcitrate, bismuth subgalate, bismuth subsalicylate, and mixtures thereof; the sulfonamides; the nitrofurans, such as nitrofurazone, nitrofurantoin, and furozolidone; and miscellaneous antibacterials such as metronidazole, tinidazole, nimorazole, and benzoic acid; and antibiotics, including the aminoglycosides, such as gentamycin, neomycin, kanamycin, and streptomycin; the macrolides, such as erythromycin, clindamycin, and rifamycin; the penicillins, such as penicillin G, penicillin V, Ampicillin and amoxicillin; the polypeptides, such as bactracin and polymyxin; the tetracyclines, such as chlorotetracycline, oxytetracycline, and doxycycline; the cephalosporins, such as cephalexin and cephalothin; and miscellaneous antibiotics, such as chloramphenicol, and clindamycin. More preferably, the antibacterial agent is selected from the group consisting of bismuth aluminate, nitrofurantoin, furozolidone, metronidazole, tinidazole, nimorazole, benzoic acid, gentamycin, neomycin, kanamycin, streptomycin, erythromycin, clindamycin, rifamycin, penicillin G, penicillin V, Ampicillin amoxicillin, bacitracin, polymyxin, tetracycline. chlorotetracycline, oxytetracycline, doxycycline, cephalexin, cephalothin, chloramphenicol, and clidamycin.

The antibacterial agent of the present invention may be used in many distinct physical forms well known in the pharmaceutical art to provide an initial dosage of the antibacterial agent and/or a further time-release form of the antibacterial agent. Without being limited thereto, such physical forms include free forms and encapsulated forms, and mixtures thereof.

The amount of antibacterial agent which may be employed in the antibacterial-wound healing therapeutic compositions of the present invention may vary depending upon the therapeutic dosage recommended or permitted for the particular antibacterial agent. In general, the amount of antibacterial agent present is the ordinary dosage required to obtain the desired result. Such dosages are known to the skilled practitioner in the medical arts and are not a part of the present invention. In a preferred embodiment, the antibacterial agent in the antibacterial-wound healing composition is present in an amount from 0.01% to about 10%, preferably from about 0.1% to about 5%, and more preferably from about 1% to about 3%, by weight.

In the preferred embodiments of applicant's invention the antifungal agent is selected from the group consisting of astemizole, chlotrimazole, omeprazole, econozole, oxiconozole, sculconazole, fluconazole, ketoconazole, itraconazole, terbinafine, and mixtures thereof.

B. Methods for Making the Antibacterial/Antifungal-wound Healing Compositions of Embodiment Two (I.A-G+X+Y)

The present invention extends to methods for making the therapeutic antibacterial/antifungal-wound healing compositions (I.A-G+X+Y). In general, a therapeutic antibacterial/antifungal-wound healing composition is made by forming an admixture of the wound healing components of Embodiment One (I.A-G) and an antibacterial agent and/or an antifungal agent. In a first aspect of Embodiment Two (I.A-G+X+Y), an antibacterial wound therapeutic composition is made by forming an admixture of an antibacterial agent, an antifungal agent, and a wound healing composition comprising (a) zinc oxide, (b) two or more fat soluble vitamins. In a second aspect of Embodiment Two (I.A-G.+X), an antibacterial-wound healing therapeutic composition is made by forming an admixture of an antibacterial agent and a wound healing composition comprising (a) zinc oxide, (b) two or more fat soluble vitamins. In a third aspect of Embodiment Two (I.A-G+Y), an antifungal-wound healing therapeutic composition is made by forming an admixture of an antibacterial agent and a wound healing composition comprising (a) zinc oxide, and (b) two or more fat soluble vitamins.

In a preferred embodiment, the invention is directed to a method for preparing a therapeutic antibacterial-wound healing composition (I.A-G+X) which comprises the steps of admixing the following ingredients:
  (A) A therapeutically effective amount of an antibacterial agent; and
  (B) a wound healing composition which comprises;
    (a) zinc oxide and;
    (b) two or more fat soluble vitamins.

C. Methods for Employing the Antibacterial/Antifungal-Wound Healing Composition Embodiment Two (I.A-G+X+Y)

The present invention extends to methods for employing the therapeutic antibacterial-wound healing compositions (I.A-G+X). In general, a therapeutic composition is employed by contacting the therapeutic composition with a wound. In a preferred embodiment, the invention is directed to a method for healing an infected wound in a mammal with an antibacterial-wound healing composition (I.A+X) which comprises the steps of:
  (A) providing a therapeutic antibacterial-wound healing composition which comprises;
    (1) a therapeutically effective amount of an antibacterial agent; and
    (2) a wound healing composition which comprises;
      (a) zinc oxide;
      (b) two or more fat soluble vitamins; and
  (B) contacting the antibacterial-wound healing composition with the infected or non-infected wound.

D. Methods for Employing the Antibacterial/Antifungal-wound Healing Composition Embodiment Two (I.A-G+Y)

The present invention extends to methods for employing the therapeutic antifungal-wound healing compositions (I.A-G+Y). In general, a therapeutic composition is employed by contacting the therapeutic composition with a wound. In a preferred embodiment, the invention is directed to a method for healing an infected wound in a mammal with an antifungal-wound healing composition (I.A-G+Y) which comprises the steps of:
  (A) providing a therapeutic antifungal-wound healing composition which comprises;
    (1) a therapeutically effective amount of an antifungal agent; and
    (2) a wound healing composition which comprises;
      (a) zinc oxide;
      (b) two or more fat soluble vitamins; and
  (B) contacting the antifungal-wound healing composition with the infected or non-infected wound.

E. Augmented Antibacterial/Antifungal-wound Healing Compositions of Embodiment Two (I.A-G+X+Y+M)

In another aspect of Embodiment Two, the therapeutic antibacterial/antifungal-wound healing compositions (I.A-G+X+Y) of the present invention may be further combined with medicaments useful for treating wounds (M) to form augmented antibacterial/antifungal-wound healing compositions (I.A-G+X+Y+M). In this embodiment, the combination of the antibacterial/antifungal-wound healing composition of the present invention and the medicament useful for treating wounds provides an augmented antibacterial-wound healing composition having an enhanced ability to increase the proliferation and resuscitation rate of mammalian cells. For example, the therapeutic compositions of the present invention may be used in combination with medicaments useful for treating wounds such as immunostimulating agents (BETAFECTIN®), antiviral agents, antikeratolytic agents, anti-inflammatory agents, antifungal agents, tretinoin, sunscreen agents, dermatological agents, topical antihistamine agents, other antibacterial agents, bioadhesive agents, respiratory bursting inhibitors (lactic acid, adenosine), inhibitors of prostaglandin synthesis (ibuprofen, aspirin, indomethacin, meclofenomic acid, retinoic acid, padimate O, melcomen, oxybenzone), steroidal anti-inflammatory agents (corticosteroids including synthetic analogs), antimicrobial agents (NEOSPORIN® ointment, silvadine), antiseptic agents, anesthetic agents (pramoxine hydorchloride, lidocaine, benzocaine) cell nutrient media, burn relief medication, sun burn medications, acne preparations, insect bite and sting medications, wound cleansers, wound dressings, scar reducing agents (Vitamin E), and the like, and mixtures thereof, to further enhance the proliferation and resuscitation rate of mammalian cells. Preferably, the medicament useful for treating wounds is selected from the group consisting of immunostimulating agents, antiviral agents, antikerotolytic agents, anti-inflammatory agents, antifungal agents, tretinoin, sunscreen agents, dermatological agents, topical antihistamine agents, antibacterial agents, bioadhesive agents, respiratory bursting inhibitors, inhibitors of prostaglandin synthesis, antimicrobial agents, cell nutrient media, scar reducing agents, and mixtures thereof. More preferably, the medicament useful for treating wounds is selected from the group consisting of immunostimulating agents, antiviral agents, antikeratolytic agents, anti-inflammatory agents, antifungal agents, acne treating agents, sunscreen agents, dermatological agents, antihistamine agents, antibacterial agents, bioadhesive agents, and mixtures thereof.

In a preferred embodiment, the invention is directed to an augmented antibacterial/antifungal-wound healing composition (I.A+X+Y+M) which comprises:
 (A) a therapeutic antibacterial/antifungal-wound healing composition which comprises:
  (1) a therapeutically effective amount of an antibacterial agent; and/or
  (2) a therapeutically effective amount of an antifungal agent; and
  (3) a wound healing composition which comprises:
   (a) zinc oxide; and
   (b) two or more fat soluble vitamins; and
 (B) a medicament useful for treating wounds.

The present invention extends to methods for making the augmented antibacterial/antifungal-wound healing compositions. In general, the augmented compositions are made by admixing the therapeutic antibacterial/antifungal-wound healing composition with the medicament useful for treating wounds to prepare the augmented antibacterial/antifungal-wound healing composition The present invention also extends to methods for employing the augmented antibacterial/antifungal-wound healing compositions. In general, an augmented antibacterial/antifungal-wound healing composition is employed by contacting the composition with a wound. In a preferred embodiment, the invention is directed to a method for healing an infected or non-infected wound in a mammal with an augmented antibacterial/antifungal-wound healing composition (I.A+X+Y+M) which comprises the steps of
 (A) providing a therapeutic augmented antibacterial/antifungal-wound healing composition which comprises:
  (1) a therapeutically effective amount of an antibacterial agent; and/or
  (2) a therapeutically effective amount of antifungal agent;
  (3) a wound healing composition which comprises:
   (a) zinc oxide; and
   (b) two or more fat soluble vitamins; and
  (4) providing a medicament useful for treating wounds; and
 (B) contacting the augmented antibacterial-wound healing composition with the infected wound.

The types of wounds which may be healed using the antibacterial/antifungal-wound healing compositions and the augmented antibacterial/antifungal-wound healing compositions of the present invention are those which result from an infected injury which causes epidermal and tissue damage. The topical therapeutic compositions may be used orally in the form of a mouth wash or spray to protect and accelerate the healing of injured oral tissue.

Methods for healing a wound comprise topically administering the compositions of the present invention directly to a wound site to increase the healing rate of the wound. The composition is maintained in contact with the wound for a period of time sufficient to increase the proliferation and resuscitation rate of the cells.

E. Formulations of the Antibacterial/Antifungal-Wound Healing Compositions of Embodiment Two (I.A-G+X+Y) and (I.A-G+X+M)

Once prepared, the inventive therapeutic antibacterial-wound healing compositions and augmented antibacterial/antifungal-wound healing compositions may be stored for future use or may be formulated in effective amounts with pharmaceutically acceptable carriers such a pharmaceutical appliances and topical vehicles (oral and non-oral) to prepare a wide variety of pharmaceutical compositions. The pharmaceutically acceptable carriers which may be employed and the methods used to prepare the pharmaceutical compositions have been described above in connection with the formulations of the wound healing compositions of Embodiment One (I.A-G).

In a preferred embodiment, the invention is directed to an antibacterial/antifungal-wound healing pharmaceutical-wound healing pharmaceutical composition which comprises:
 (A) a therapeutic antibacterial-wound healing composition (I.A-G+X+Y) which comprises:
  (1) a therapeutically effective amount of an antibacterial agent; and
  (2) a therapeutically effective amount of an antifungal agent; and
  (3) a wound healing composition which comprises:
   (a) zinc oxide; and
   (b) two or more fat soluble vitamins; and
 (B) a pharmaceutically acceptable carrier selected from the group consisting of pharmaceutical appliances, bioadhesives, and occlusive vehicles.

In another preferred embodiment, the invention is directed to a method for preparing a pharmaceutical composition for increasing the proliferation and resuscitation rate of mammalian cells, which comprises the steps of.
 (A) providing a therapeutically effective amount of an antibacterial/antifungal-wound healing composition (I.A-G+X+Y) which comprises:
  (1) an antibacterial agent; and
  (2) an antifungal agent; and
  (3) a wound healing composition comprising
   (a) zinc oxide
   (b) two or more fat soluble vitamins; and
 (B) providing a pharmaceutically acceptable carrier; and
 (C) Admixing the antibacterial/antifungal-wound healing composition from step (A) and the pharmaceutically acceptable carrier from step (B) to form a pharmaceutical composition.

What is claimed is:

1. A method of healing skin wounds in mammals by repairing skin tissue in mammals, comprising topically contacting a mammalian skin wound to be treated with a therapeutic composition consisting essentially of:

2 to 25 wt % zinc oxide;

vitamin A, vitamin D, vitamin E, and vitamin K, wherein the four vitamins are present in a combined amount of 1 to 35 wt %; and an effective antimicrobial amount of bacitracin zinc and an effective antifungal amount of clotrimazole.

2. The method of claim 1, wherein said Vitamin A is selected from the group consisting of retinol, 3,4-didehydroretinol, carotene, alpha-carotene, beta-carotene, delta-carotene, and gamma carotene.

3. The method of claim 1, wherein said Vitamin D is selected from the group consisting of cholecalciferol and ergocalciferol.

4. The method of claim 1, wherein said Vitamin E is selected from the group consisting of Vitamin E acetate, Vitamin E succinate, pharmaceutically acceptable Vitamin E salts and Vitamin E phosphate.

5. The method of claim 1, wherein said Vitamin A is retinal palmitate.

6. The method of claim 1, wherein said Vitamin D is ergocalciferol.

7. The method of claim 1, wherein said Vitamin E is tocopherol.

* * * * *